(12) United States Patent
Cooper

(10) Patent No.: US 7,837,674 B2
(45) Date of Patent: Nov. 23, 2010

(54) COMPACT COUNTER BALANCE FOR ROBOTIC SURGICAL SYSTEMS

(75) Inventor: Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 972 days.

(21) Appl. No.: 11/627,934

(22) Filed: Jan. 26, 2007

(65) Prior Publication Data

US 2007/0156122 A1    Jul. 5, 2007

Related U.S. Application Data

(63) Continuation-in-part of application No. 11/043,688, filed on Jan. 24, 2005, now Pat. No. 7,763,015.

(51) Int. Cl.
*E04G 3/00* (2006.01)
*G05G 5/00* (2006.01)

(52) U.S. Cl. ............... 606/1; 248/284.1; 248/280.11; 74/589

(58) Field of Classification Search ............... 606/1; 248/284.1, 280.11
See application file for complete search history.

(56) References Cited

U.S. PATENT DOCUMENTS

| | | | |
|---|---|---|---|
| 1,638,938 A | 8/1927 | Koenigkramer | |
| 1,644,231 A | 10/1927 | Bosworth | |
| 2,076,446 A | 4/1937 | Carwardine | |
| 2,090,439 A | 8/1937 | Carwardine | |
| 2,131,693 A | 9/1938 | Smith | |
| 2,287,577 A | 6/1942 | Stava | |
| 2,416,910 A | 3/1947 | Crosby | |
| 2,547,532 A | 4/1951 | Medelsohn | |
| 2,700,524 A | 1/1955 | Lauterbach | |
| 2,941,776 A | 6/1960 | Lauterbach | |
| 3,000,606 A | 9/1961 | Storm | |
| 3,041,060 A | 6/1962 | Jacobsen | |
| 3,122,348 A | 2/1964 | Wilkinson | |
| 3,374,347 A | 3/1968 | Hirose | |

(Continued)

FOREIGN PATENT DOCUMENTS

DE    19742050 A1    3/1999

(Continued)

OTHER PUBLICATIONS

PCT/US08/051206, Invitation to Pay Additional Fees including a Partial International Search Report, 4 pages.

(Continued)

*Primary Examiner*—Henry M Johnson, III
*Assistant Examiner*—Jeffrey B Lipitz

(57) ABSTRACT

In one embodiment of the invention, an apparatus is provided including a linkage and a balancing mechanism coupled to the linkage around a pivotal joint. The linkage couples to a support structure at a first end and support a weight applied to a second end. The balancing mechanism counter balances the weight applied to the second end of the linkage. As the linkage is deformed to vertically adjust the height of the weight with a different moment arm length, the balancing mechanism varies a cable path length to modify the compression of a spring and a tension in a cable to adjust the amount of counter balance force applied to the linkage.

33 Claims, 20 Drawing Sheets

U.S. PATENT DOCUMENTS

| | | |
|---|---|---|
| 3,426,190 A | 2/1969 | Bobrick |
| 3,476,931 A | 11/1969 | Fletcher |
| 3,547,390 A | 12/1970 | Mehr |
| 3,584,793 A | 6/1971 | Ilzig |
| 3,713,453 A | 1/1973 | Chiaro |
| 3,820,752 A | 6/1974 | Oram |
| 3,856,251 A | 12/1974 | Miller |
| 3,883,105 A | 5/1975 | Matsumoto |
| 4,080,530 A | 3/1978 | Krogsrud |
| 4,107,769 A | 8/1978 | Saluja |
| 4,160,536 A | 7/1979 | Krogsrud |
| 4,165,530 A | 8/1979 | Sowden |
| 4,166,602 A | 9/1979 | Nilsen |
| 4,266,747 A | 5/1981 | Souder |
| 4,437,144 A | 3/1984 | Guenther |
| 4,494,177 A | 1/1985 | Matthews |
| 4,517,632 A | 5/1985 | Roos |
| 4,523,732 A | 6/1985 | Biber |
| 4,744,019 A | 5/1988 | Krogsrud |
| 4,770,384 A | 9/1988 | Kuwazima |
| 5,025,359 A | 6/1991 | Saluja |
| 5,186,337 A | 2/1993 | Foster |
| 5,333,103 A | 7/1994 | Cvek |
| 5,340,072 A | 8/1994 | Halbirt |
| 5,348,260 A | 9/1994 | Acevedo |
| 5,445,166 A | 8/1995 | Taylor |
| 5,609,316 A | 3/1997 | Tigliev |
| 5,618,090 A | 4/1997 | Montague |
| 6,012,821 A | 1/2000 | Yeaney |
| 6,246,200 B1 | 6/2001 | Blumenkranz et al. |
| 6,788,018 B1 | 9/2004 | Blumenkranz |
| 6,821,259 B2 | 11/2004 | Rahman et al. |
| 2004/0261179 A1 | 12/2004 | Blumenkranz |

FOREIGN PATENT DOCUMENTS

| | | |
|---|---|---|
| EP | 0024433 A | 3/1981 |
| WO | WO 03-099152 | 12/2003 |

OTHER PUBLICATIONS

"A Simple Technique to Passively Gravity Balance Articulated Mechanisms", Tariq Rahman, Transcript of the ASME J. of Mechanical Design, 1995.

Herder, J.L., "Theory, conception and design of statically balanced spring mechanisms," Internet: <http://mms.tudelft.nl/staff/herder/statbal.htm> Downloaded May 21, 2008.

PCT/US08/51206 International Search Report and Written Opinion of the International Searching Authority, mailed Sep. 16, 2008, 17 pages.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

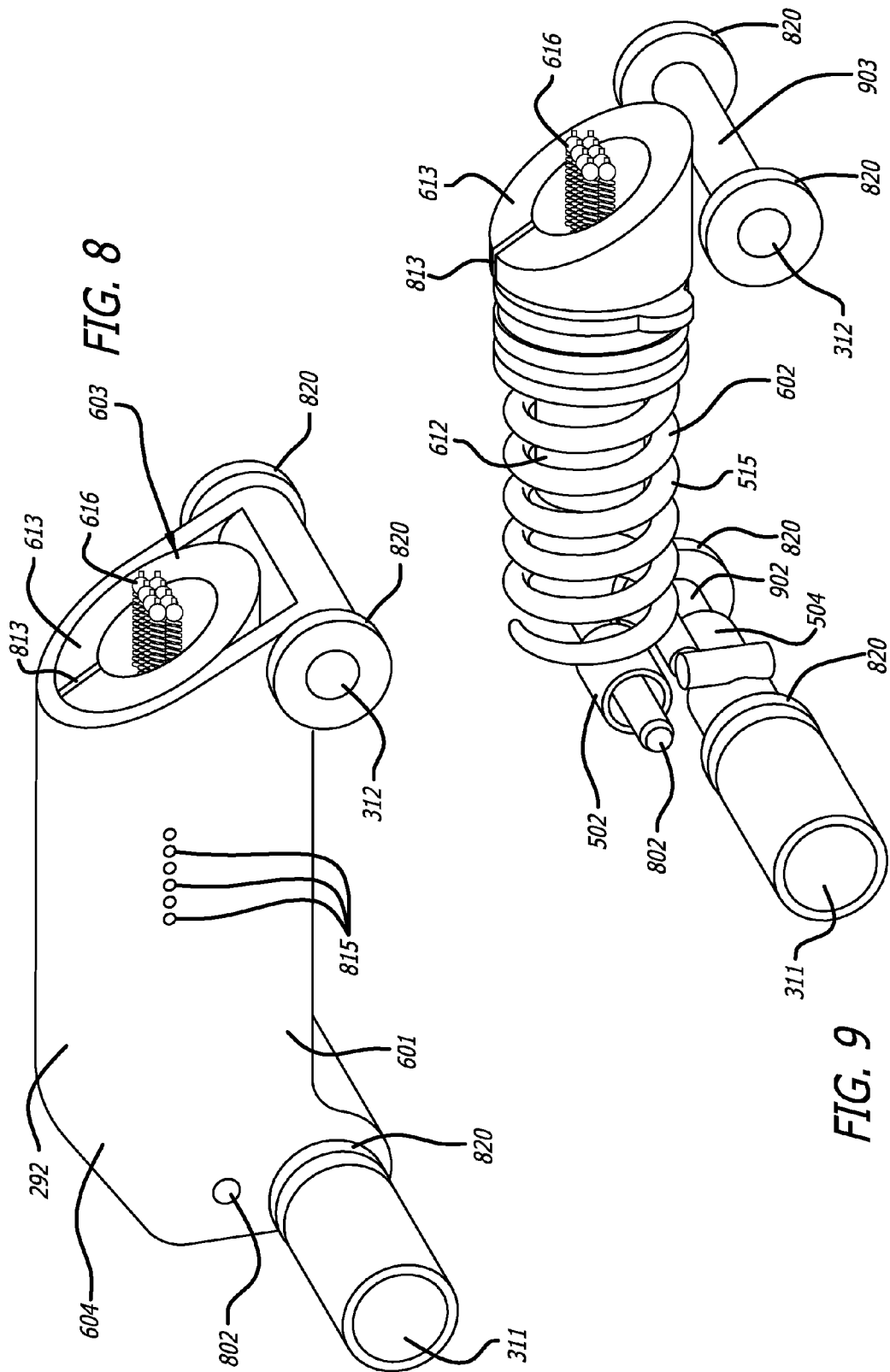

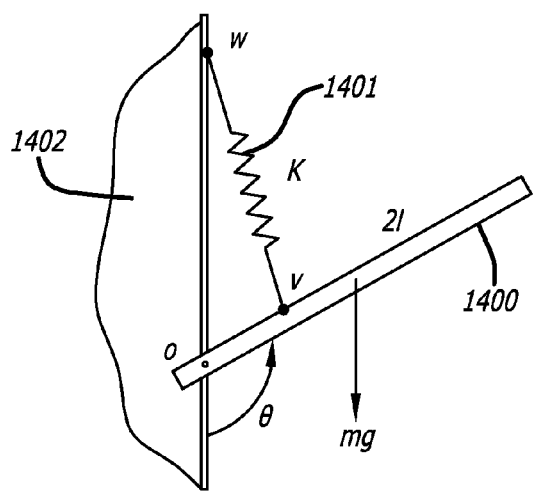
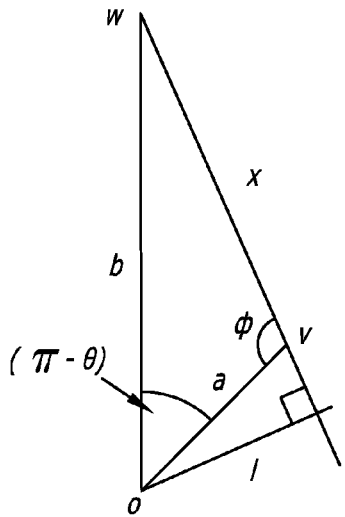
FIG. 14A        FIG. 14B
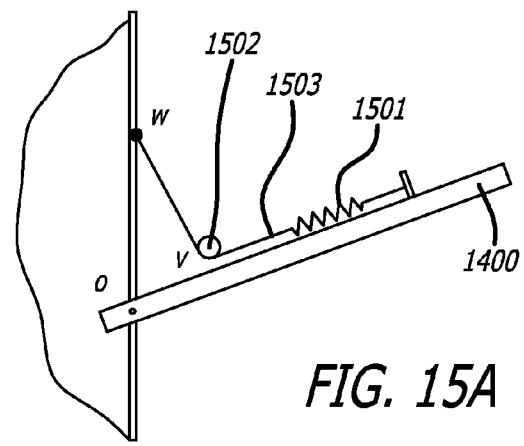
FIG. 15A
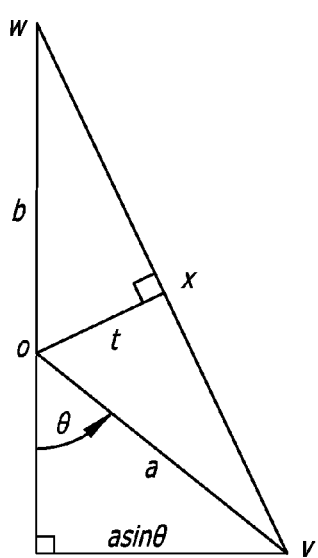
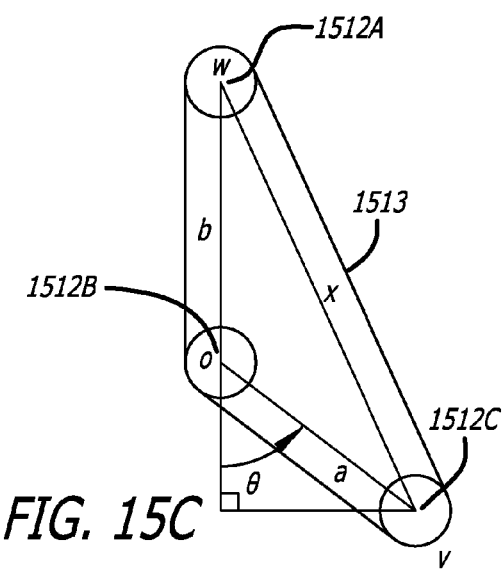
FIG. 15B        FIG. 15C

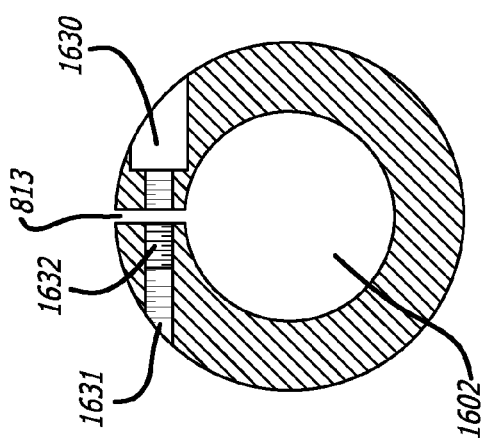
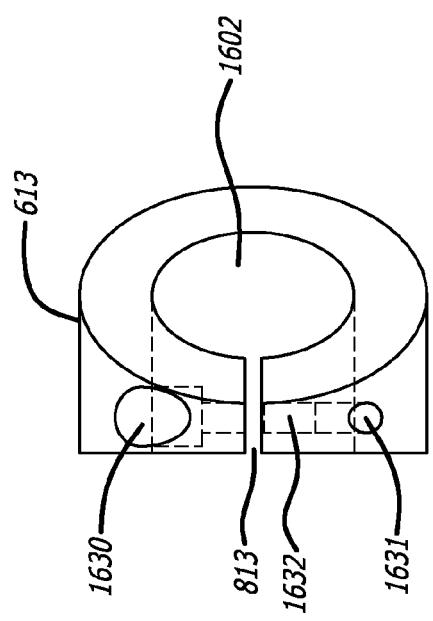
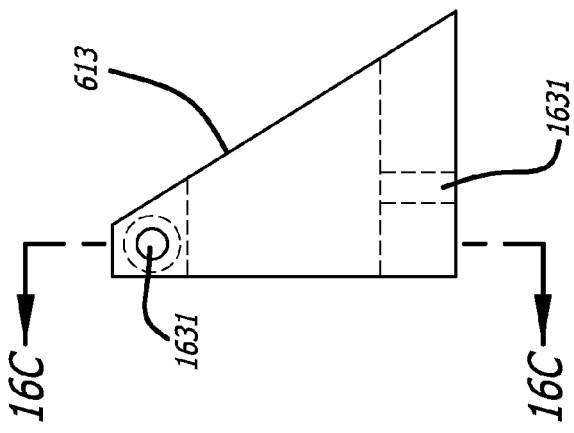

US 7,837,674 B2

COMPACT COUNTER BALANCE FOR ROBOTIC SURGICAL SYSTEMS

CROSS-REFERENCE TO RELATED APPLICATIONS

This non-provisional United States (U.S.) patent application claims the benefit of and is a continuation-in-part (CIP) of U.S. patent application Ser. No. 11/043,688 filed on Jan. 24, 2005 by inventors Thomas G. Cooper, et al., entitled "MODULAR MANIPULATOR SUPPORT FOR ROBOTIC SURGERY", pending, which is incorporated herein by reference.

FIELD

The present invention is generally related to robotic surgical systems. More specifically, the embodiments of the invention are related to counter balancing systems for robotic surgical arms.

BACKGROUND OF THE INVENTION

Previously, robotic surgical arms of robotic surgical systems were supported over a patient by mounting the robotic surgical arms to a patient's table or by mounting them to a patient side cart that was wheeled over the floor to the patient.

A patient side cart takes up floor space and typically requires cables routed along the floor between a master console and the patient side cart. The cords are easy to trip upon. Moreover, the patient side cart and the robotic surgical system require a set-up procedure. Sometimes instead to being at a patient's side, the patient side cart is positioned at the head or feet of the patient. After the surgery is completed, the patient side cart is moved out of the way. A patient side cart is heavy and difficult to move.

Additionally, while off the floor, mounting the robotic surgical arms to a patient's table typically limits the range of motion and the types of surgeries that may be performed. Robotic surgical arms may be mounted to either or both sides of the patient's table. However when mounted to the table, the robotic surgical arms are often limited in range of motion to avoid bumping one another.

It is desirable to mount the robotic surgical arms over a patient without cluttering the operating room floor while maintaining a significant range of motion in robotic surgical arms.

BRIEF SUMMARY OF THE INVENTION

The embodiments of the invention are summarized by the claims that follow below.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIG. 8 is a perspective view of the compact counter balance link.

FIG. 9 is a perspective view of the compact counter balance link with the hollow housing removed.

FIG. 14A is a diagram of a spring counter balancing mechanism for a link.

FIG. 14B is a schematic diagram of the spring counter balancing mechanism of FIG. 14A.

FIG. 15A is a diagram of a spring, pulley, and cable counter balancing mechanism for a link.

FIGS. 15B-15C are schematic diagrams of the spring, pulley, and cable counter balancing mechanism of FIG. 15A.

FIGS. 16A-16C are views of the end plug that is inserted into the cavity to provide additional stiffness to the counter balancing link.

DETAILED DESCRIPTION OF THE INVENTION

Figure 1:
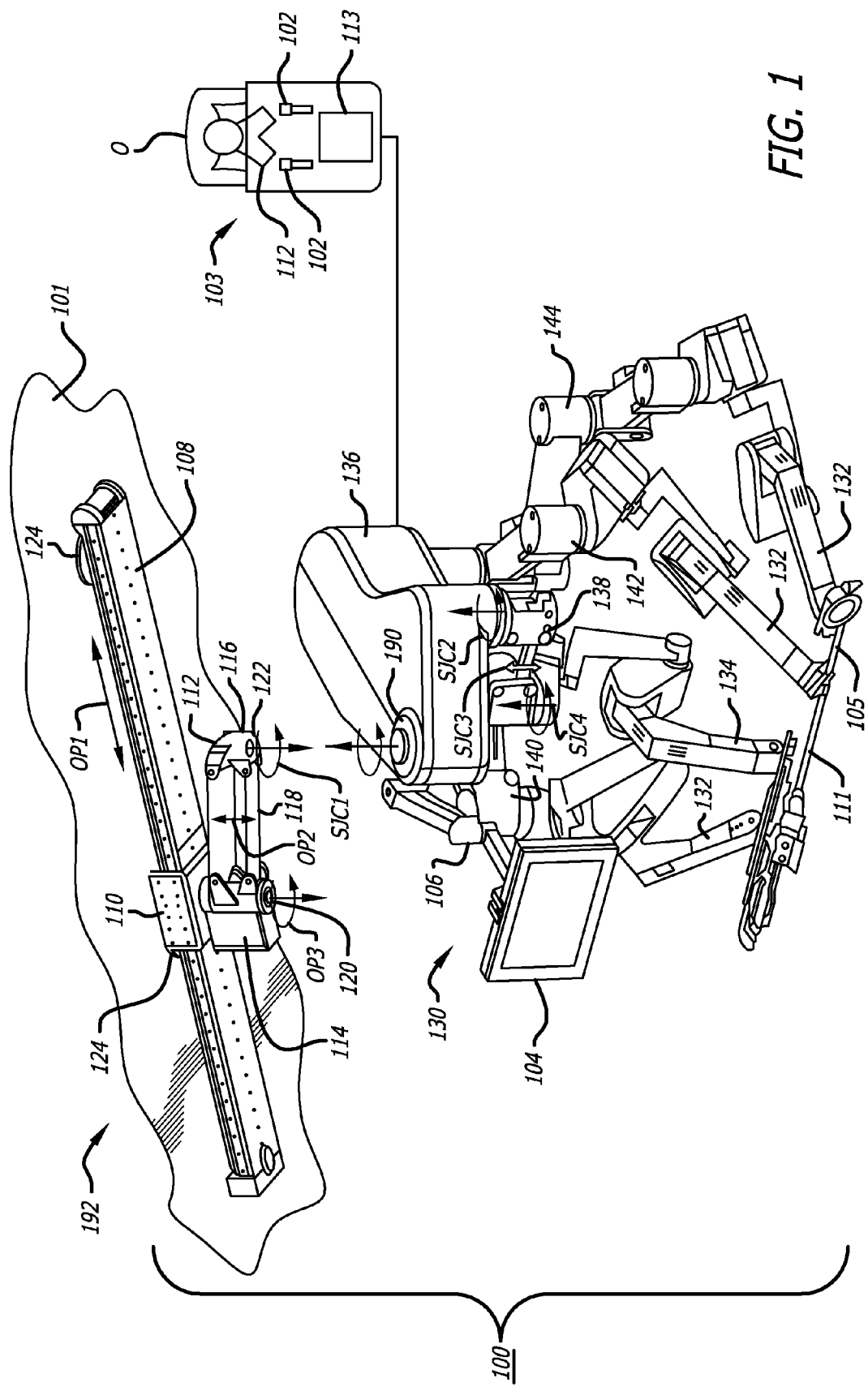
FIG. 1 is a perspective view of a robotic surgical system, including a master surgeon console or workstation for inputting a surgical procedure and a ceiling mounted robotic cart, including positioning linkages which allow a plurality of patient side robotic manipulators for robotically moving surgical instruments having surgical end effectors at surgical sites, one endoscope camera robotic manipulator, and a monitor to be pre-configured.

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and elements have not been described in detail so as not to unnecessarily obscure aspects of the embodiments of the invention.

In one embodiment of the invention, a set-up arm is provided to support a robotic arm. The set-up arm includes a first set-up joint to couple to a support structure, a second set-up joint to couple to a robotic arm to provide support thereto; an idle link pivotally coupled between the first set-up joint and the second set-up joint, a counter balancing link coupled between the first set-up joint and the second set-up joint, a third pulley coupled to the counter balancing link between the counter balancing link and the first set-up joint, and at least one cable under tension wrapped over the first, second, and third pulleys, and coupled to the set up arm. The center points of the first pulley, the second pulley, and the third pulley form a triangle. The first set-up joint has a bracket with the first pulley rotatably coupled thereto. The counter balancing link generates a counter-balancing force to balance out a force of the weight or load at the second set-up joint. The counter balancing link includes a hollow housing having a cylindrical cavity with a first diagonally cut end forming an oval opening to increase stiffness. The counter balancing link further includes the second pulley rotatably coupled to the housing, the post coupled to the housing, and a first compression spring in the cylindrical cavity of the housing with its first end coupled to the housing. The first compression spring is under compression to balance out the force of weight at the second set-up joint. The at least one cable under tension is coupled to a second end of the first compression spring near its end.

In another embodiment of the invention, a method for a set-up arm of a robotic surgical system is provided. The method includes balancing a linkage structure with a spring-cable-pulley balancing mechanism to support a weight or load; moving the linkage structure to vary the moment of a weight at a pivot point when the weight is at the end of a link; and changing a path length of one or more cables over a plurality of pulleys in the spring-cable-pulley balancing mechanism to compress or decompress a spring to increase or decrease tension in the one or more cables to balance the variance in the moment.

In yet another embodiment of the invention, a counter-balanced arm is provided including a first link, a second link pivotally coupled to the first link at a first pivot point, a third pulley rotatably coupled between the second link and the first link at the first pivot point, and a cable coupled to the second link, routed over the third pulley, the first pulley, and the second pulley. The first link can couple to a support mechanism at a first end. The first link has the first pulley rotatably coupled thereto. The second link has the second pulley rotatably coupled thereto. The second link further has a first compression spring having a first end coupled thereto. The cable is further coupled to a second end of the first compression spring to form a tension in the cable to counter balance a weight applied at an end of the second link.

In still another embodiment of the invention, an apparatus is provided including a linkage and a spring-cable-pulley balancing mechanism coupled to the linkage around a pivotal joint. The linkage couples to a support structure at a first end and support a weight at a second end. The spring-cable-pulley balancing mechanism counter balances the weight at the second end of the linkage. As the linkage is deformed to vertically adjust the height of the weight with a different moment arm length, the spring-cable-pulley balancing mechanism varies a cable path length to modify the compression of a spring and a tension in a cable to adjust the amount of counter balance force applied to the linkage.

Ceiling Mounted Robotic Surgical System

Referring now to FIG. 1, a robotic surgical system 100 is illustrated including a perspective view of an exemplary modular manipulator support assembly 130, a platform linkage 192, and a surgeon's console 103. The platform linkage 192 may couple to a ceiling 101 or overhead support structure by means of a pair of brackets 124. The modular manipulator support assembly 130 is slidingly coupled to the platform linkage 192.

An operator O (generally a surgeon) performs a minimally invasive surgical procedure on a patient lying on an operating table T under the modular manipulator support assembly 130 and the platform linkage 192. The operator O manipulates one or more input devices or masters 102 at the surgeon's console 103. In response to the surgeon's inputs, a computer processor 113 of console 103 directs movement of endoscopic surgical instruments or tools 105, effecting servo-mechanical movement of the instruments via the modular manipulator support assembly 130. The image of the internal surgical site is shown to surgeon or operator O by a stereoscopic display viewer 112 in the surgeon's console 103, and is simultaneously shown to assistant A by an assistant's display 104. Assistant A assists in pre-positioning the manipulators 132, 134 relative to patient P using set-up linkage arms 138, 140, 142, 144; in swapping tools 105 of the one or more of surgical manipulators for alternative surgical tools or instruments; and in operating related non-robotic medical instruments and equipment, and the like.

The modular manipulator support assembly 130 aligns and supports robotic manipulators, such as patient side manipulators 132 or endoscope camera manipulator 134, with a set of desired surgical incision sites in a patient's body. The modular manipulator support assembly 130 generally includes an orienting platform 136 and a plurality of configurable set-up joint arms 138, 140, 142, 144 coupleable to the orienting platform 136. Each arm 138, 140, 142, 144 is movably supporting an associated manipulator 132, 134 which in turn movably supports an associated instrument. It will be appreciated that the depictions are for illustrative purposes only and do not necessarily reflect the actual shape, size, or dimensions of the modular manipulator support assembly 130. This applies to all depictions described hereinafter.

In general terms, the arms or linkages 138, 140, 142, 144 comprise a positioning linkage or set-up arm portion of system 100, typically remaining in a fixed configuration while tissue is manipulated, and the manipulators 132, 134 comprise a driven portion which is actively articulated under the direction of surgeon's console 103. The manipulators 132, 134 are primarily used for master/slave tissue manipulation, while the set-up arms 138, 140, 142, 144 are used for positioning and/or configuring the manipulators 132, 134 before use, when repositioning the patient, operating table, incision points, and the like.

For convenience in terminology, manipulators 132 actuating tissue with surgical tools 195 is sometimes referred to as a PSM (patient side manipulator), and a manipulator such as 134 controlling an image capture or data acquisition device, such as endoscope 111, is sometimes referred to as an ECM (endoscope-camera manipulator), it being noted that such telesurgical robotic manipulators may optionally actuate, maneuver and control a wide variety of instruments, tools and devices useful in surgery.

The orienting platform 136 generally supports a plurality of set-up joint arms SJA1 140, SJA2 142, and SJX 144 for movably supporting the associated patient side manipulators 132. Typically, each arm accommodates translation of the patient side manipulator in three dimensions (x, y, z) and rotation of the patient side manipulator about one vertical axis (azimuth). Generally, the set up joint arms 140, 142, and 144 support robotic surgical arms or patient side manipulators (PSM). Either or both of the right and left surgeon controls 102 may flexibly drive the robotic surgical arms or patient side manipulators coupled to the set-up joint arms 140, 142, and 144. The surgeon O may select and switch between which arm he is controlling with the master controls 102 such as by using a foot pedal.

The orienting platform 136 further supports one set-up joint center arm 138 (SJC) for movably supporting the endoscope camera manipulator 134. It will be appreciated that the set-up arms 138, 140, 142, 144 may interchangeably support and position instrument 132 or camera 134 manipulators.

Utilization of the orienting platform 136 to support the individually positionable set-up arms 138, 140, 142, 144 and associated manipulators 132, 134 advantageously results in a simplified single support unit having a relatively scaled down, compact size. For example, the single orienting platform 136 may obviate any need to individually arrange and mount each set-up arm 138, 140, 142, 144 to a mounting base, which is often confusing and cumbersome. This in turn allows for a faster and easier set-up.

The orienting platform 136 may further include a display 104. The display 104 may be used for set-up purposes, instrument changes, and/or for personnel viewing of a procedure. The display 104 is preferably adjustably mounted to the orienting platform 136 with a parallelogram linkage 106 so that personnel can view the monitor in a desired direction. The platform linkage 192 movably supports the orienting platform 136 at a fifth hub 190. That is, the fifth hub 190 is coupleable to the platform linkage 192. The fifth hub 190 may be aligned with the pivot point of the set-up joint center arm 138, which is preferably coincident with its incision site for the endoscope. The fifth hub 190 provides for rotation of the orienting platform 136 about a vertical axis as denoted by arrow SJC1 in FIG. 1. Rotation of the orienting platform 136 about the pivot point of the endoscope manipulator 134 which is aligned with the surgical incision advantageously allows for increased maneuverability of the orienting platform 136 and associated set-up arms 138, 140, 142, 144 in the direction in which a surgical procedure is to take place. This is of particular benefit during complex surgeries, as manipulator 132, 134 positioning may be varied mid-operation by simply rotating the orienting platform 136 about the fifth hub 190. Typically, the instruments will be retracted prior to rotation for safety purposes. For small rotations of the orienting platform 136 or tilting of the operating table, the low friction and balanced arms 140, 142, 144 may float while attached to the cannula during movement, pushed by force from the incisions.

Rotation of the orienting platform 136 about hub 190 (SJC 1), rotation of the set-up joint arms 140, 142 about hubs (SJA1 1), and rotation of the set-up joint auxiliary arm 144 about a hub are preferably power operated, but may alternatively be manual or computer controlled. Motors driving belt and pulley mechanisms for orienting platform rotation (SJC 1) are within the orienting platform 136. A brake system may also be included to allow the orienting platform 136 to be locked into place. Motors driving belt and pulley mechanisms for right, left, and auxiliary set-up arm rotation (SJA11, SJX1) 140, 142, 144 respectively may also be contained within the orienting platform 136.

The platform linkage 192 generally comprises a linear rail 108, a slideable carriage 110 coupleable to the rail 108, and at least one arm 112 rotationally coupleable to the carriage 110 on a proximal end 114 and to the orienting platform 136 via hub 190 on a distal end 116. The platform linkage 192 advantageously enhances maneuverability of the modular manipulator support 130 by accommodating translation of the orienting platform 136 in three dimensions (x, y, z). Movement of the orienting platform in a generally horizontal direction is denoted by arrow OP1. Movement of the orienting platform in a generally vertical direction is denoted by arrow OP2. Movement of the orienting platform in and out of the page is articulated by rotational movement of joint 120, as denoted by arrow OP3. The platform linkage 192 further accommodates rotation of the orienting platform 136 about one vertical axis, as denoted by arrow SJC 1. The arm 112 preferably comprises a four bar parallelogram linkage 118 extending between a pair of adjacent joints 120, 122. It will be appreciated that although the fifth hub 190 accommodates rotation of the orienting platform 136 (SJC1), the system may also be designed wherein the fifth hub 190 is rotationally coupleable to the platform linkage 192 so that the platform linkage accommodates pivotal motion of the orienting platform.

The orienting platform's 136 enhanced range of motion due to the platform linkage 192 permits access to incision sites over a wide range of the patient's body. This of particular benefit when performing complicated and lengthy procedures, where the manipulators 132, 134 may be quickly repositioned mid-operation to alternative surgical sites. Typically, the instruments will be retracted prior to translation or rotation of the orienting platform 136 for safety purposes. The platform linkage 192 is preferably power operated, but may alternatively be manual or computer controlled. Motors may be located within the platform linkage 192 or orienting platform 136 to drive pulley and belt mechanisms. A brake system may also be included to allow the platform linkage 192 to be locked into place.

The platform linkage 192 may be mounted to a mounting base (not shown) via bolts and brackets 124 or other conventional fastener devices. The mounting base preferably comprises a ceiling-height support structure that may be coupled to the ceiling 101 so as to permit the manipulator support assembly 192, 130 to extend generally downward from the base. A ceiling-height mounted manipulator support assembly 192,130 advantageously improves space utilization in an operating room, particularly clearing up space adjacent the operating table for personnel and/or other surgical equipment as well as minimizing robotic equipment and cabling on the floor. Further, a ceiling-height mounted manipulator support assembly minimizes the potential for collisions or space conflicts with other adjacent manipulators during a procedure and provides for convenient storage when the robotic surgery system is not in use.

The term "ceiling-height support structure" includes support structures disposed on, adjacent, or within an operating room ceiling and includes support structures disposed substantially below an actual ceiling height, especially in the case of a higher-than-typical operating room ceiling. The mounting base permits the manipulator support assembly 192, 130 to be stored by pulling it against the wall. The mounting base may include existing architectural elements, such as original or reinforced structural elements, joists, or beams. Further, the mounting base may be formed from sufficiently rigid and stiff materials to inhibit vibration. Alternatively, passive means such as viscous or elastomer dampers or active means such as servomechanisms may be used to counteract vibration or interfloor movement of the hospital building in vertical and/or horizontal directions.

Set-Up Joint Arms and Robotic Surgical Arms

Each set-up joint arm 138, 140, 142, 144 has simplified kinematics due to the improved range of motion provided by the manipulators 132, 134. Typically, the arms accommodate translation of the fixable links and joints in a generally vertical direction such as denoted by arrow SJC3 for arm 138 in FIG. 1 and arrow SJA13 for arm 140 in FIGS. 2E,2G. The arms also accommodate rotation of the fixable links and joints about two or three vertical axes.

Figure 2B:
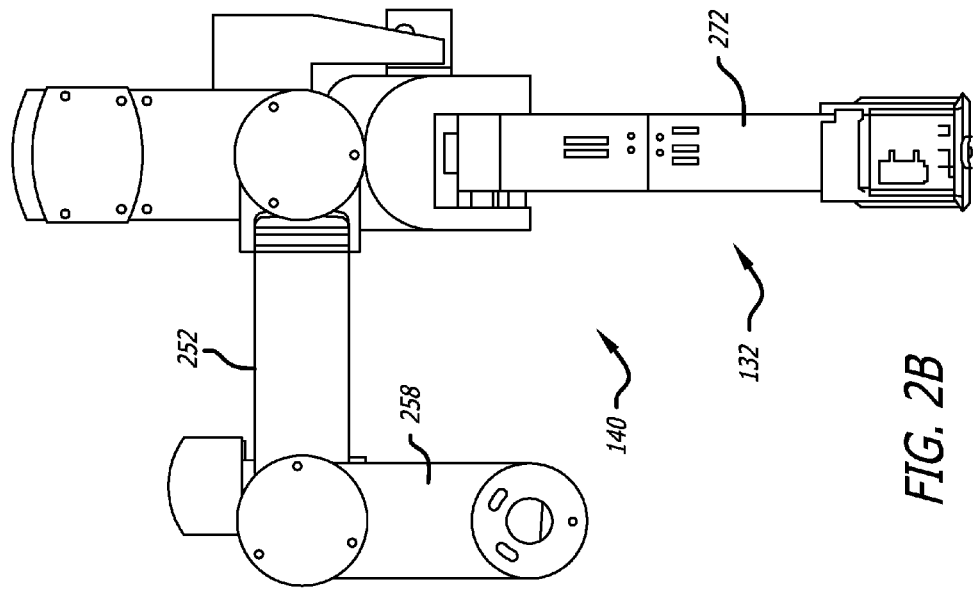
FIGS. 2A through 2H illustrate perspective and top views of the set-up joint arm supporting and positioning a robotic patient side manipulator or robotic surgical arm.
Figure 2A:
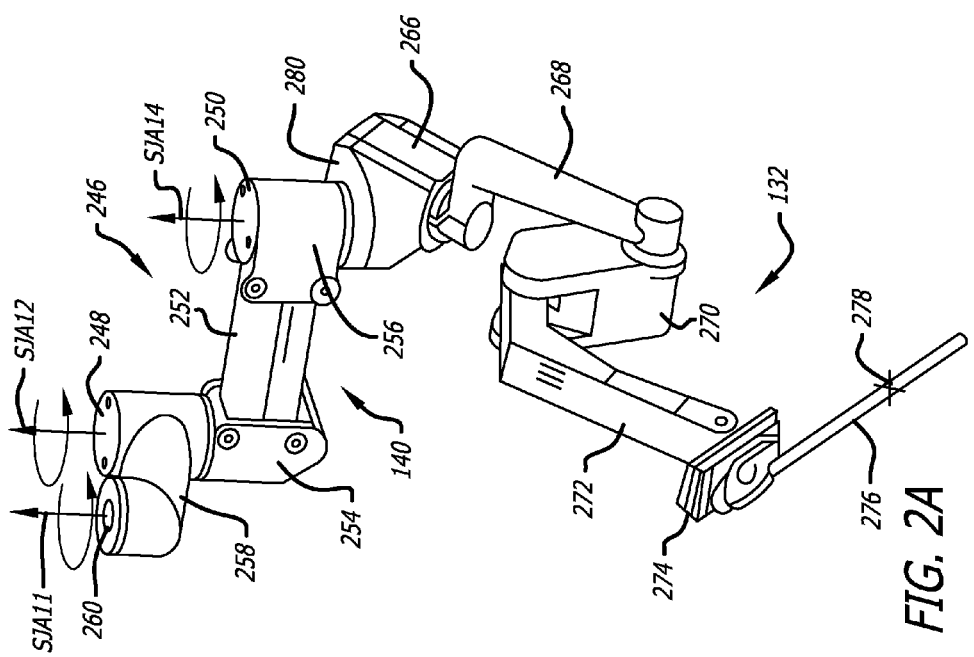
Figure 2C:
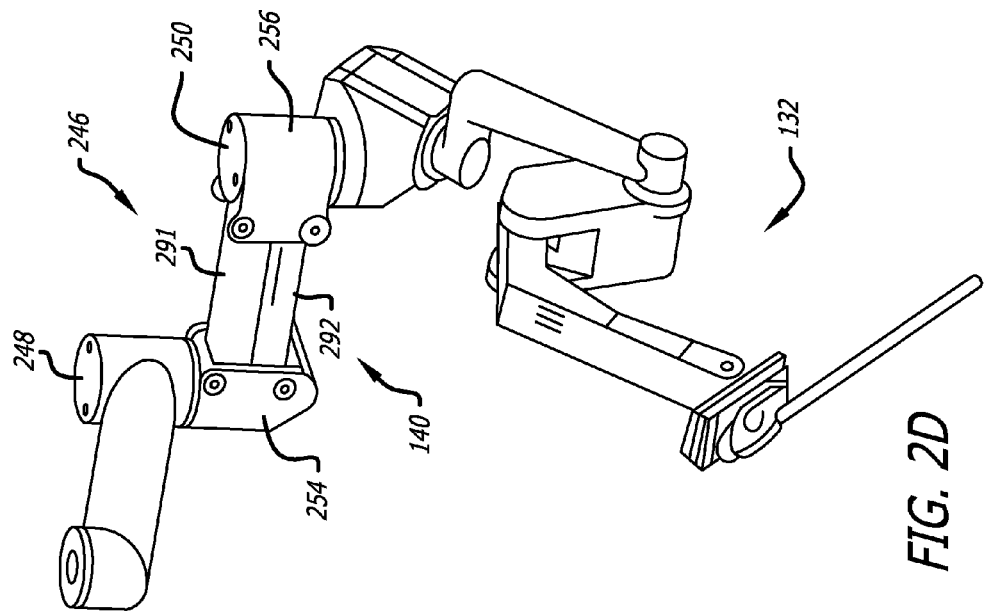
Figure 2D:
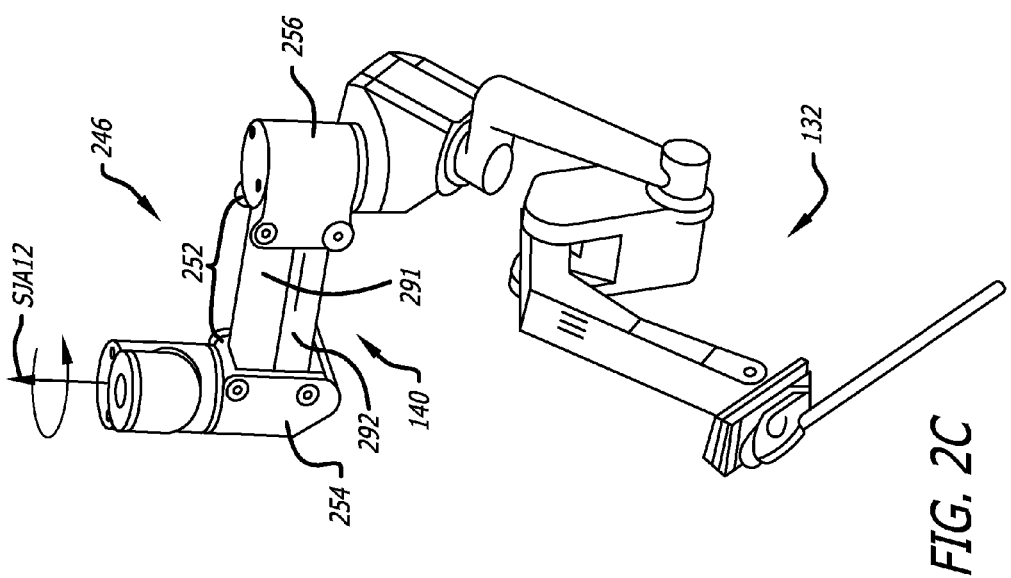
Figure 2F:
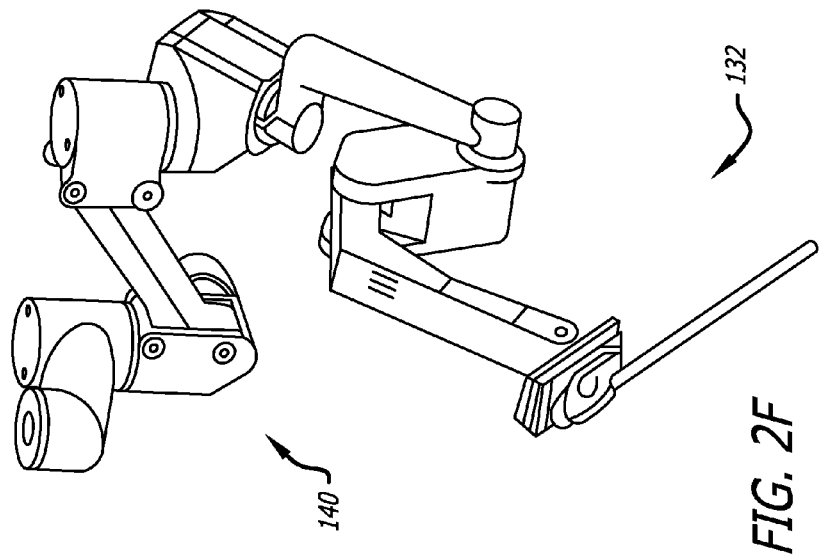
Figure 2E:
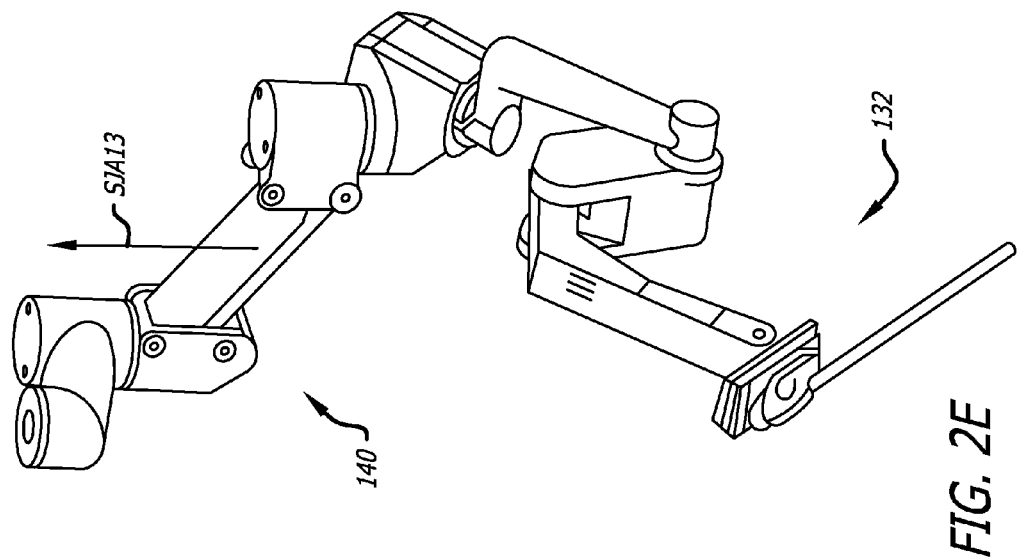
Figure 2H:
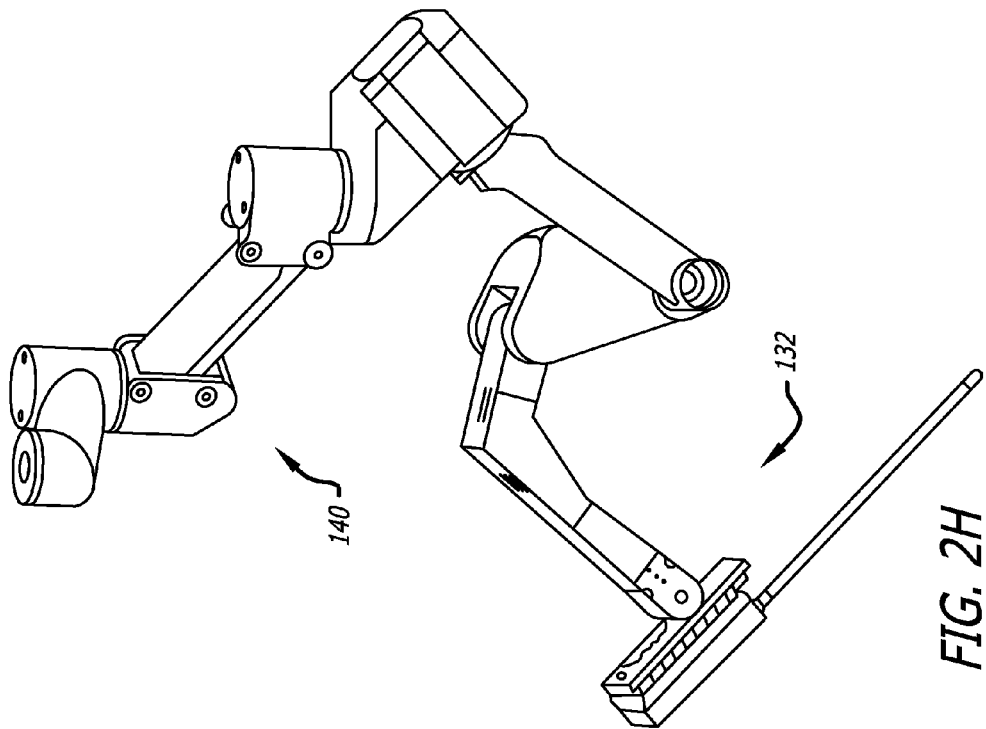
Figure 2G:
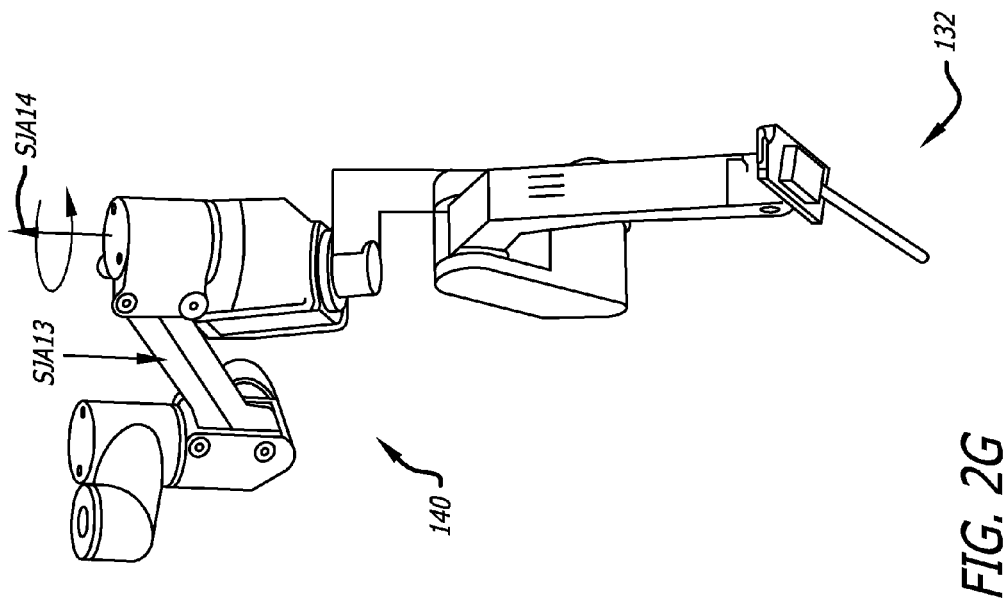

Referring now to FIGS. 2A-2H, an exemplary set-up joint arm 140 and patient side manipulator 132 are illustrated. Set-up joint arm 140 is exemplary of each of the other set-up joint arms 138, 142, 144. Patient side manipulator 132 is exemplary of the endoscopic camera manipulator 140. Top views of the set-up joint arm 140 supporting the patient side robotic manipulator 132 are shown by FIGS. 2A-2B. The set-up joint arm 140 has four degrees of freedom (SJA11, SJA12, SJA13, SJA14), wherein the SJA11 joint is motorized and the other joints are manually positioned. FIGS. 2C and 2D illustrate rotational motion of the set-up joint arm 140 as denoted by arrow SJA12. FIGS. 2E and 2F illustrate both translational and rotational motion of the set-up joint arm 140 as denoted by arrows SJA13, and SJA14. The translational and rotational axes for the left set-up joint arm 142 (SJA2) is substantially similar to that of the right set-up joint arm 140 (SJA1).

As seen in FIG. 2A, arrows SJA11, SJA12, and SJA14 illustrate the rotational joints 260, 248, 250 respectively of the set-up joint arm 140. The translational and rotational axes for the left set-up joint arm 142 (SJA2) are substantially similar to that of the right set-up join arm 140 (SJA1).

The set up joint arms 138, 140, 142, 144 may be power operated, computer controlled, manually pre-configured, or a combination thereof. Preferably, joint SJA11 of the set-up joint arm 140 is motorized while the other joints are manually positioned. Motors may be located within the plurality of fixable links or orienting platform to drive pulley and belt mechanisms.

The fixable joints of the set-up arms 138, 140, 142, 144 typically include a brake system to allow the joints to be locked into place after the arms are appropriately deployed. In FIG. 2A, the brake system releasably inhibits articulation of the fixable links 252, 258, and joints 248, 250, previously configured in at least substantially fixed configuration. The brake system is preferably biased toward the fixed configuration and includes a brake release actuator for releasing the fixable links 252, 258 and joints 248, 250 to a repositionable configuration in which the fixable links and joints can be articulated. The system may further include a joint sensor system coupling a plurality of the fixable links 252, 258 and joints 248, 250 to a servomechanism. The sensor system generates joint configuration signals. The servomechanism includes a computer and the joint sensor system transmits the joint configuration signals to the computer. The computer calculates a coordinate system transformation between a reference coordinate system affixed relative to a mounting base and the instruments using the joint configuration signals.

Referring now to FIG. 1 and FIG. 2A, the manipulators 132, 134 are mechanically constrained so that a manipulator base 266 is at a fixed angle relative to horizontal. The manipulator 132 supported by the set-up joint arm 140 is angularly offset relative to horizontal in a range from forty degrees to about sixty degrees, preferably from about forty-five degrees to about fifty degrees. The manipulator 132 supported by the set-up joint auxiliary arm 144 is angularly offset relative to horizontal in a range from zero degrees to about twenty degrees, preferably by about fifteen degrees. The manipulator 134 supported by the set-up joint center arm 138 is angularly offset relative to horizontal in a range from forty degrees to about ninety degrees, preferably from about sixty-five degrees to about seventy degrees.

Preferably, the manipulators 132, 134 comprise offset remote center linkages for constraining spherical pivoting of the instrument about pivot points 278 in space, wherein actuation of the fixable links and joints of the set-up joint arms 138, 140, 142, 144 moves the pivot points. As discussed above, the overall complexity of the robotic surgical system may be reduced due to the improved range of motion of the system. Specifically, the number of degrees of freedom in the set-up joints arms 138, 140, 142, 144 may be reduced (e.g., less than six degrees of freedom). This allows for a simpler system platform requiring less pre-configuration of the set-up joint arms 138, 140, 142, 144. As such, operating room personnel may rapidly arrange and prepare the robotic system for surgery with little or no specialized training.

Exemplary manipulators 132, 134 providing for reduced mechanical complexity of the set-up arms 138, 140, 142, 144 are described in further detail in U.S. patent application Ser. No. 10/957,077, which is incorporated herein by reference.

In FIG. 2A, the offset remote center manipulator 132 generally includes the manipulator base 266, a parallelogram linkage base 268, a plurality of driven links and joints 270, 272, and an instrument holder 274. The manipulator base 266 is rotationally coupled to the parallelogram linkage base 268 for rotation about a first axis, also known as the yaw axis. The parallelogram linkage base 268 is coupled to the instrument holder 274 by rigid links 270, 272 coupled together by rotational pivot joints. The driven links and joints 270, 272 define a parallelogram so as to constrain an elongate shaft of the instrument or cannula 276 relative to a center of rotation (also referred to as a pivot point) 278 when the instrument is mounted to the instrument holder 274 and the shaft is moved along an insertion axis. The first axis and a first side of the parallelogram adjacent the parallelogram linkage base 268 intersect the shaft at the center of rotation 278, wherein the first side of parallelogram is angularly offset from the first axis.

The manipulator base 266 of the surgical manipulators 132, 134 is mounted and supported at a constant elevation angle by set-up arms 138, 140, 142, 144. The manipulator base 266 in this embodiment is fixed to a manipulator base support 280 of the set-up arms 138, 140, 142, 144 by screws or bolts. Although the exemplary set-up arms 138, 140, 142, 144 have a manipulator base support 280 suited to the geometry of a remote center manipulator 132, 134, manipulator base support 280 may take on a variety of alternative support configurations to suit other telesurgical manipulators. For example, the manipulator base support may be configured to support further alternative remote center manipulators, natural center manipulators, computed center manipulators, software center manipulators, and manipulators employing a combination of these functional principles. Further, as noted above, the manipulator base support 280 of the set-up arms 138, 140, 142, 144 may interchangeably support and position instrument 132 or camera 134 manipulators.

In operation, once the motorized joint position SJA11 is set, typically to preset values, the user has only to align each remote center of the patient side manipulator with each incision. This may be done by attaching each patient side manipulator to the associated cannula which is already positioned within the incision. This automatically sets the set-up joint positions, as there is no remaining redundancy. The low friction and balancing of these three joints allows the patient side manipulators to float so that each manipulator can be controlled by holding it advantageously at a single point. Setting a motorized joint to a different position will result in a different azimuth angle for the patient side manipulator after the cannula is attached. In other words, the function of the redundant, motorized joint is to allow the patient side manipulator to be farther from or closer to another patient side manipulator or endoscope manipulator. Alternatively, after the cannula is attached, the azimuth can be adjusted by operating the motor while the set-up joint brakes are released and the cannula is held at the incision.

Compact Counter Balancing Mechanism

Each of the set-up joint arms 138, 140 142, 144 defines releasably fixable links and joints that are pre-configurable.

Each set-up joint arm 138, 140, 142, 144 includes at least one balanced, fixable, jointed parallelogram linkage structure 246 extending between a pair of adjacent fixable rotational joints 248, 250. The set-up joint arms 138, 140, 142, 144 may be balanced by a variety of mechanisms including weights, tension springs, gas springs, torsion springs, compression springs, air or hydraulic cylinders, torque motors, or combinations thereof. In a preferred embodiment of the invention, a compact counter balancing mechanism is provided to balance the weight of the set-up joint arms and a robotic surgical arm, such as the patient side manipulators 132 and endoscopic camera manipulator 134. Changes in tools or instruments 105 at the end of patient side manipulators 132 typically has no effect on the counter balancing mechanism as the weight of the tool or instruments is usually insignificant.

As shown in FIG. 2A, the set-up joint arm 140 includes the balanced, fixable, jointed parallelogram linkage structure 246 extending between a pair of adjacent fixable rotational joints 248, 250. The jointed parallelogram linkage structure 246 accommodates motion in a generally vertical direction, and the adjacent rotational joints 248, 250 accommodate pivotal motion about vertical axes SJA12, SJA14. One or more linear or curved sliding axes could be used in lieu of any or all of the rotary ones. Each of the parallelogram linkage structures in the set-up joint arms may have a generally similar structure to the parallelogram linkage structure 246, in this example comprising a parallel link 252 (including an upper link or idle link 291 and a horizontal or counter balancing link 292), a proximal bracket 254, and a distal bracket 256. The proximal bracket 254, and the distal bracket 256 may also be referred to as proximal and distal ends respectively of the parallel link 252.

The parallel link 252 is pivotally jointed to proximal and distal brackets 254, 256 respectively in a vertically-oriented planar parallelogram configuration. This permits pivotal motion of the parallel link 252 in the vertical plane, while constraining the brackets 254, 256 to remain substantially parallel to one another as the parallelogram linkage structure 246 deforms or changes shape. As discussed previously, the rotational set-up joints 248, 250 and their respective brackets 254,256 accommodate pivotal motion about the vertical axes SJA12, SJA14, respectively. Thus, the parallel link 252 and the bracket 254 may pivot in a horizontal plane about the set-up joint 248 and its axis SJA12.

As illustrated by FIGS. 2C-2D, the parallel link 252 includes the upper link or idle link 291 and the horizontal link or counter balancing link 292 pivotally coupled between and to the brackets 254,256. The idle link 291, the counter balancing link 292, and the brackets 254,256 form the parallelogram linkage structure 246. The bracket 256, rotational joint 250, and the manipulator 132 can move vertically with respect to the bracket 254 and rotational joint 248 as illustrated by arrows SJA13 in FIGS. 2E and 2G.

Figure 3:
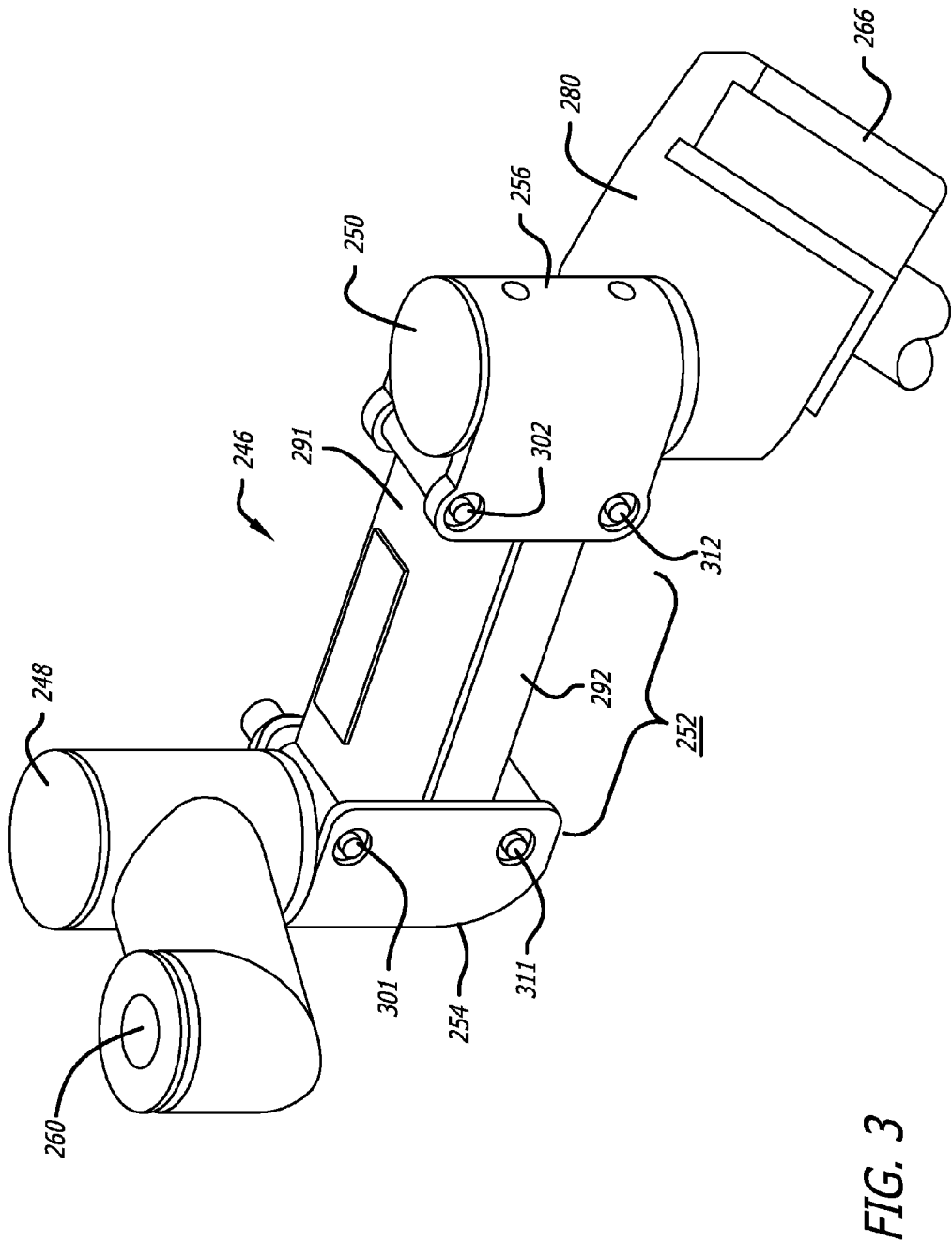
FIG. 3 is a right side perspective view of a first set-up arm with a compact counter balance mechanism.

FIG. 3 illustrates a right side magnified perspective view of the parallelogram linkage structure 246 including the idle link 291, the counter balancing link 292, the proximal bracket 254, and the distal bracket 256. As shown in FIG. 3, the idle link 291 is pivotally coupled to the proximal bracket 254 at a pivotal joint 301 and to the distal bracket 256 at a pivotal joint 302. The counter balancing link 292 is pivotally coupled to the proximal bracket 254 at a pivotal joint 311 and to the distal bracket 256 at a pivotal joint 312. The pivotal joints 301,311, 302,312 are located at the corners of the parallelogram linkage structure 246.

Figure 4:
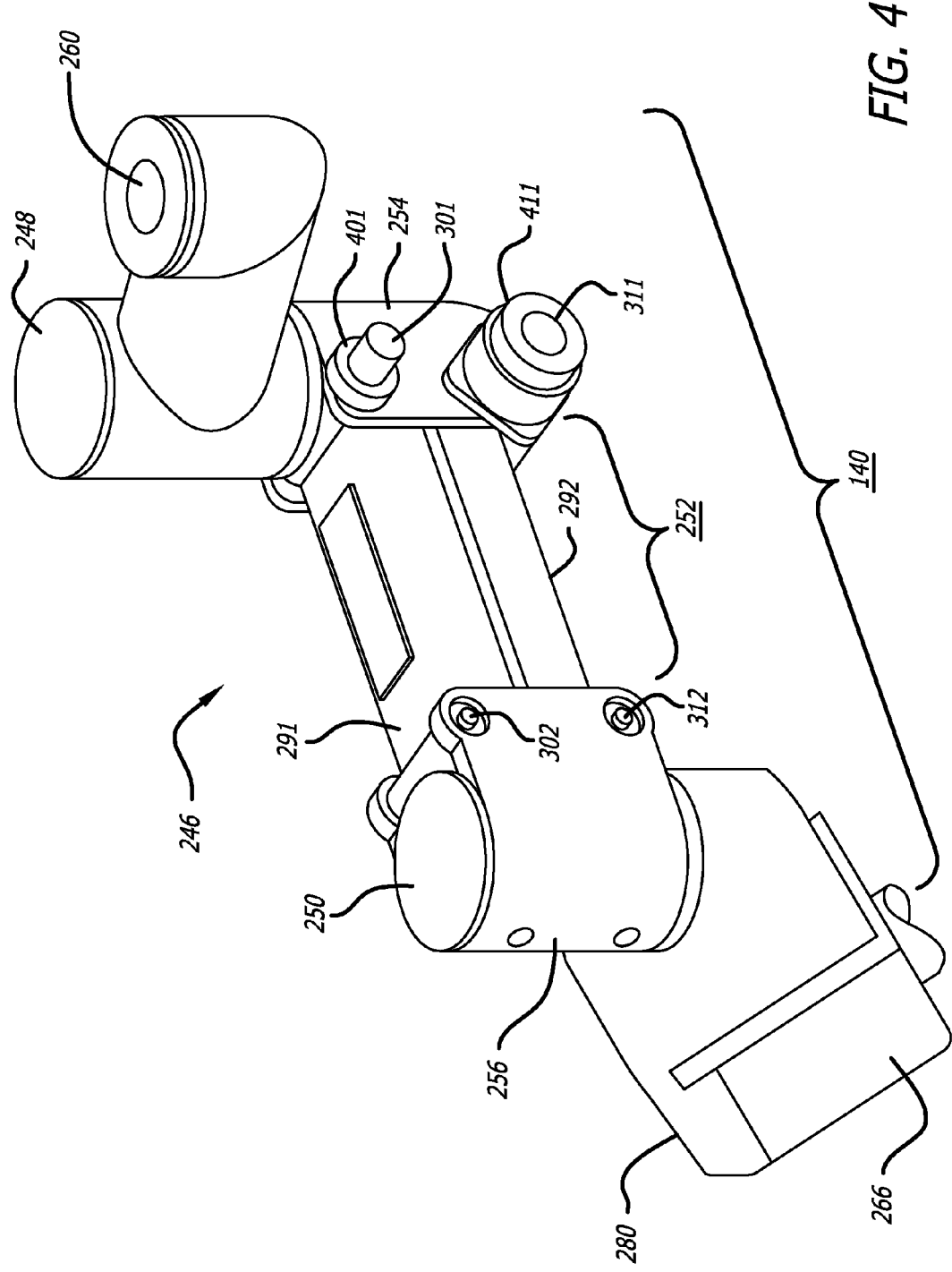
FIG. 4 is a left side perspective view of the first set-up arm with the compact counter balance mechanism.

FIG. 4 illustrates a left side magnified perspective view of the parallelogram linkage structure 246 of the set up joint arm 140. In one embodiment of the invention, the set-up joint arm 140 couples to a ceiling height support structure through the joint 260.

At joint 301 between the bracket 254 and the idle link 291, the set up joint arm 140 includes a potentiometer 401 to measure the position of the parallelogram linkage structure 246. At joint 311 between the bracket 254 and the counter balancing link 292, the set up joint arm 140 includes a set-up joint brake 411. When engaged, the set-up joint brake 411 at the joint 311 can hold the position of the parallelogram linkage structure 246.

Figure 5:
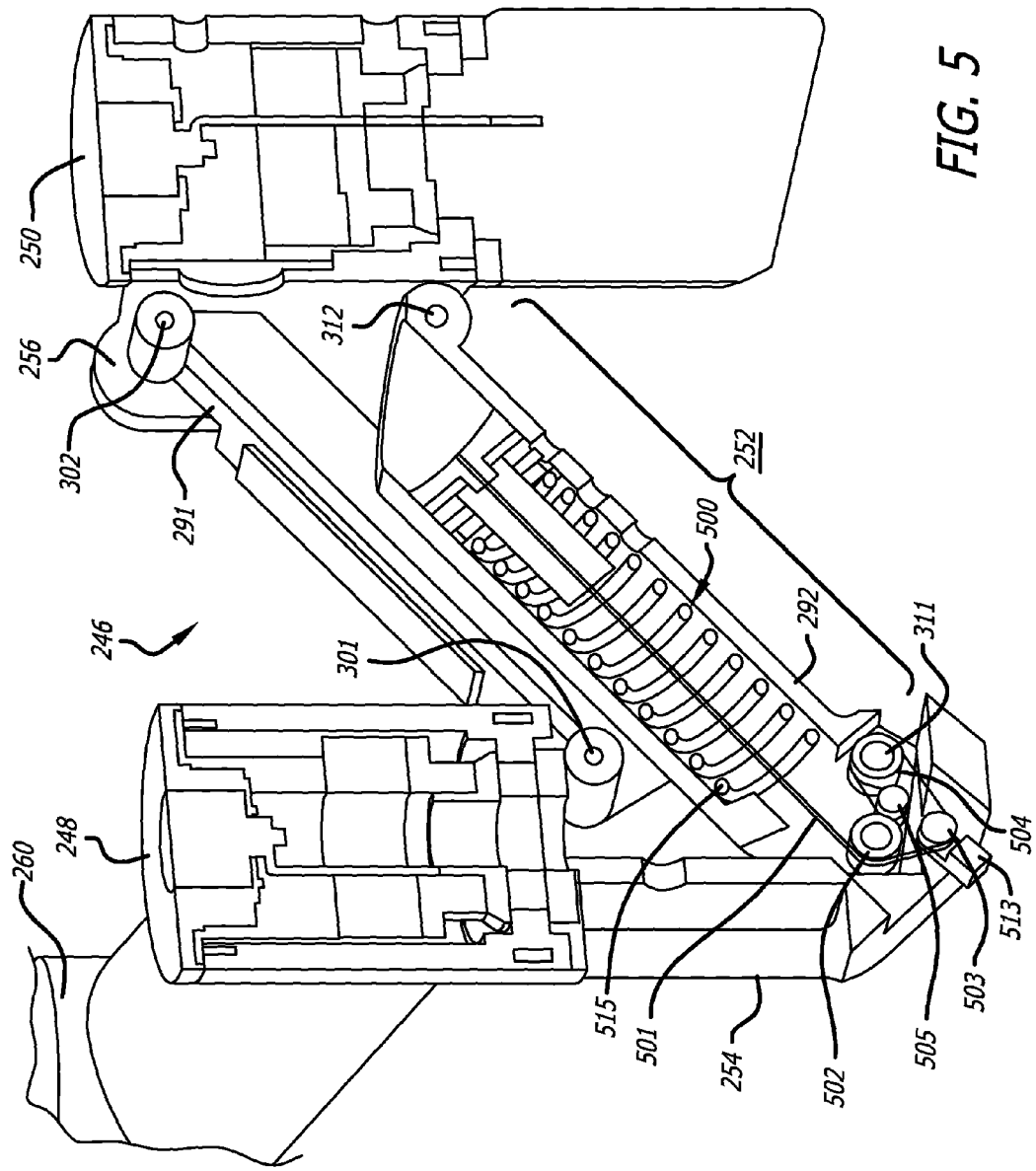
FIG. 5 is a right side cutaway view of the first set-up arm with the compact counter balance mechanism.

FIG. 5 illustrates a cutaway view of the parallelogram linkage structure 246 including the idle link 291, the counter balancing link 292, the proximal bracket 254, and the distal bracket 256. The counter balancing link 292 includes a substantial portion of the spring-cable-pulley balancing mechanism 500 that generally operates around the pivotal joint 311.

The spring-cable-pulley balancing mechanism 500 includes one or more cables 501 coupled to the set-up arm that are wrapped over a plurality of pulleys 502-504 and tensioned by a compressible spring assembly 602. The one or more cables 501 may couple to the set-up arm by coupling to the set-up joints or the counter balancing link 292. In one embodiment of the invention, the one or more cables 501 may have segments that wrap over the plurality of pulleys 502-504 in one direction, wrap around a pin or post 505 to couple to the counter balancing link, and then route back and wrap over the pulleys 502-504 in a reverse direction. Wrapping the one or more cables around the pin or post 505 in this manner is a convenient way to have segments of a single cable act like a redundant pair of cables. Alternatively one end of each of the one or more cables may be clamped to the pin or post 505 or coupled to the set-up arm, the counter balancing link 292, or one or the set-up joints by some other coupling mechanism. At least one end of each of the one or more cables 501 is clamped to an end of a compression spring 515 of the compressible spring assembly 602.

In one embodiment of the invention, the compression spring 515 is a coil spring. A compression spring is considered safer than a tension spring for a number of embodiments of the invention. If a tension spring breaks, the ends may fly apart and it would then be unable to provide any load to balance out any weight. On the other hand, if a compression coil spring breaks, the coil at the broken point will move slightly to rest on the next coil in the spring. This slight movement may only change the load by a small amount (e.g., 5-10%), which may be computed by multiplying the space between coils by the spring rate.

In one embodiment of the invention, there are four cables 501 under tension that wrap over post 505 making a U-turn so that eight cable segments are coupled to the end of the spring 515. In one embodiment of the invention, there is a total tension of approximately four-hundred-eighty pounds for all of the eight cable segments such that each substantially shares sixty pounds of tension.

In one embodiment of the invention, the plurality of pulleys 502-504 are of equal diameter. Each of the pulleys 502-504 and the post 505 may include one or more tracks in which the one or more cables 501 are wrapped and guided to substantially maintain their alignment. Pulley 504 is concentric with the pivotal joint 311 coupling to a shaft at the pivotal joint. With the one or more cables 501 wrapped over it, the pulley 504 does not rotate relative to the counter balancing link 292. However, the counter balancing link 292 and the pulley 504 rotate together about the pivotal joint 311 with respect to the bracket 254. Pulley 503 is rotationally coupled to an adjustable mount 513 that is coupled to the bracket 254. The adjustable mount 513 may slide in the bracket 254 to adjust the position of pulley 503 and further adjust the tension in the cable 501 and spring 515 during set-up and maintenance. Changing the length of one of the sides of the triangle (sides a or b in the theory described below), adjusts the counter-balancing mechanism for variations in spring rate or the amount of weight being balanced. However, the adjustable mount 513 is rigidly fixed in placed during operational periods so that the position of the pulley 503 rotatably coupled to the adjustable mount 513 does not change. Pulley 502 is rotationally coupled to the housing of the link 292 and thus pivots with the link about the pivotal joint 311. The center points or center point positions of the pulleys 502-504 are the corners or vertices of a triangle.

Figure 6A:
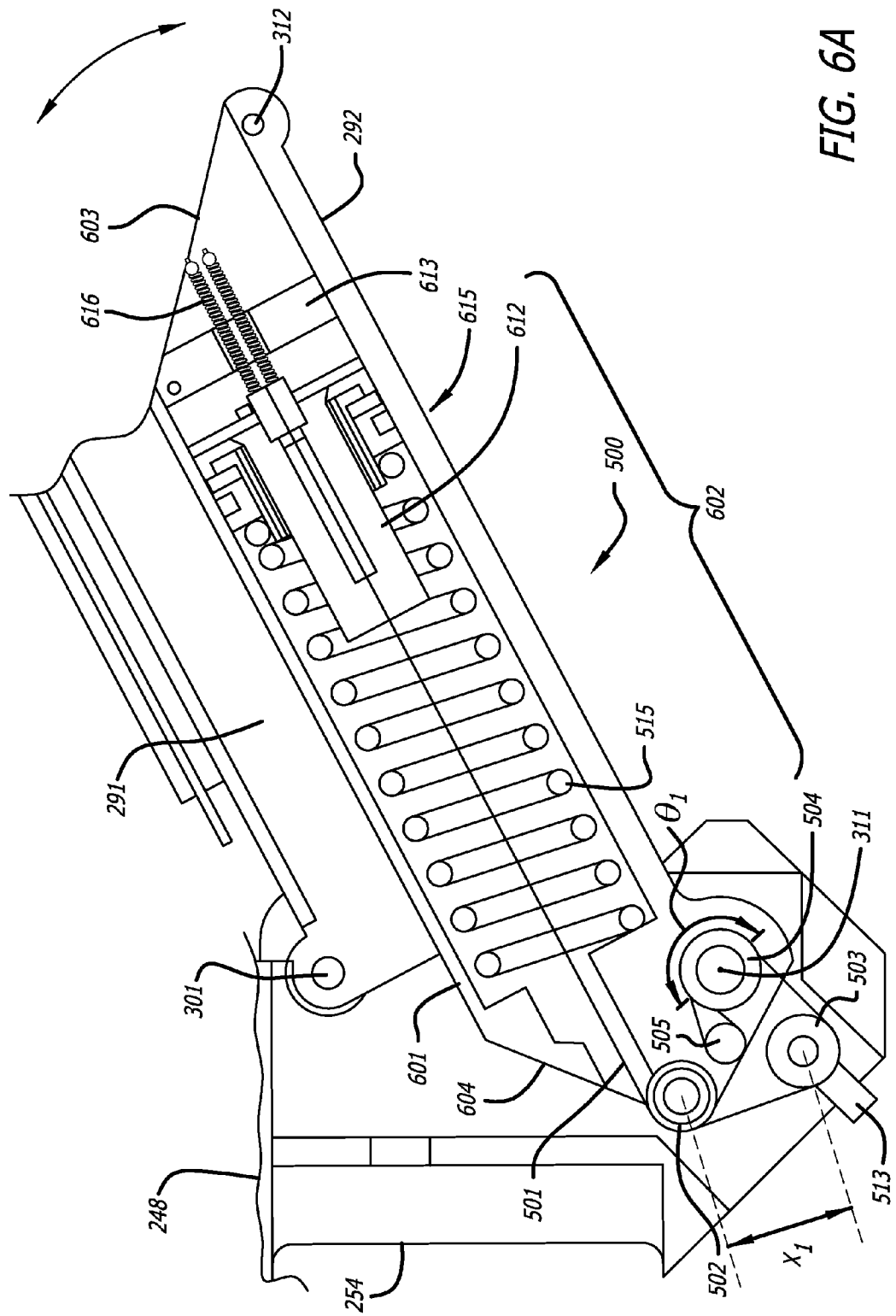
FIGS. 6A-6B are right side magnified cutaway views of the compact counter balance mechanism in an angular position and a horizontal position.
Figure 6B:
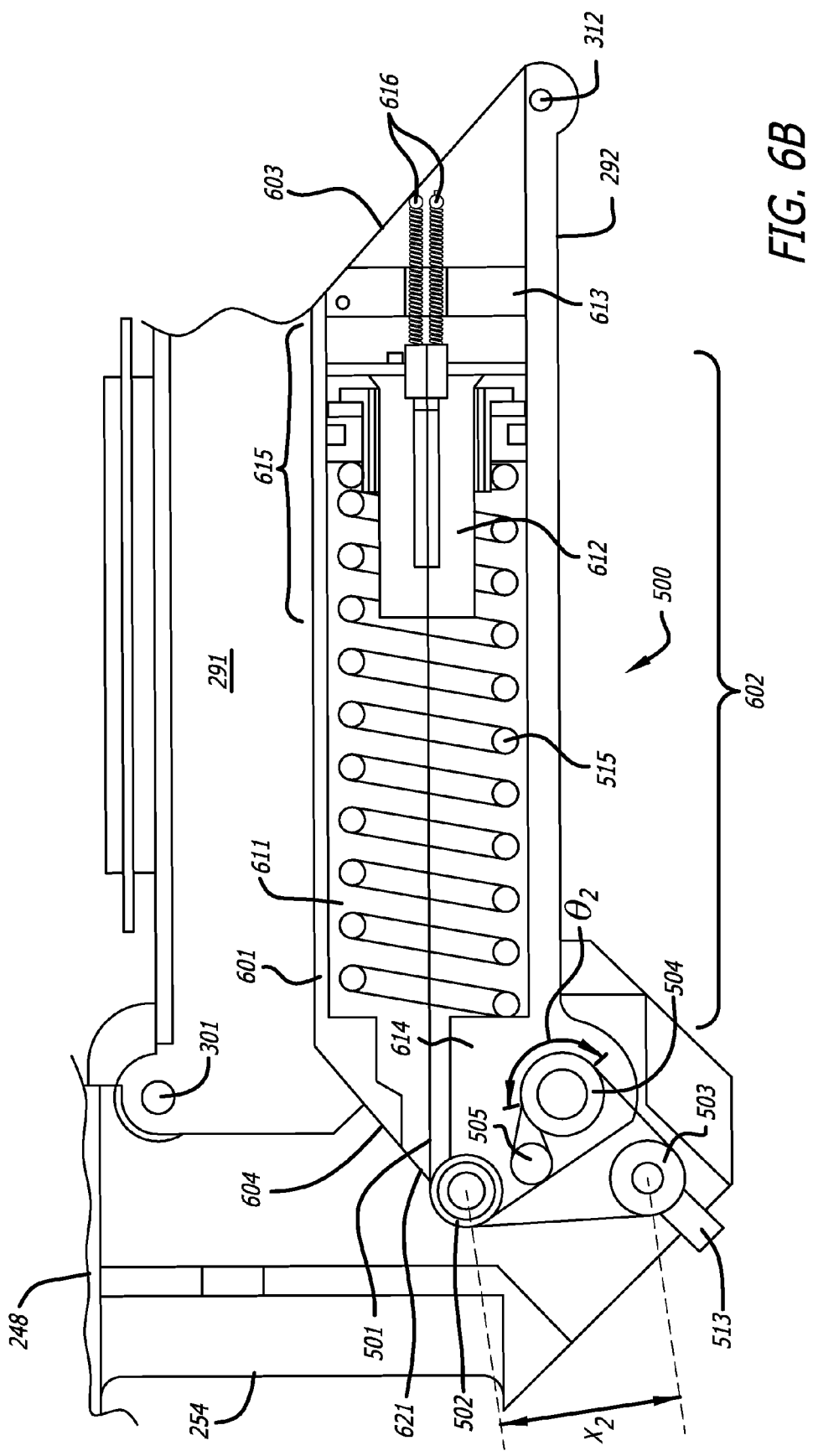

Referring now to FIGS. 6A-6B, magnified cutaway views of the counter balancing link 292 and the counter balancing mechanism 500 in differing positions are illustrated. The link 292 includes a hollow housing 601 with a cylindrical cavity 611 to receive the compressible spring assembly 602. In one embodiment of the invention, the cylindrical cavity 611 is a circular cylindrical cavity. Including the compressible spring assembly 602 in the link 292 makes for a more compact counter balancing mechanism. The housing 601 of the link 292 has a slanted or diagonally cut end 603 to allow for movement against the bracket 256 and the joint 250 while maintaining the strength of the link. The slanted end 603 also provides an oval opening into the cavity 611 through which the spring assembly 602 may be assembled. The housing 601 of the link 292 also has an opposite slanted or diagonally cut end 604 to allow for movement against the bracket 254 and the joint 248 while maintaining the strength of the link.

In some applications, such as medical or robotic surgical systems, it is desirable to make the parallelogram linkage structure stiff so that a substantially solid supporting structure may be provided. This is useful in preventing undesired vibrations that may be excited by movement, such as from movements in the robotic arm. Referring momentarily to FIG. 5, the pivotal joints 301, 311 at one end and the pivotal joints 302, 312 at an opposite end are positioned so as to be widely spaced apart with respect to the housing of the links 291, 292. That is, the pivotal joints of the idle link are located near the top outside portion of the link and the pivotal joints of the counter balancing link are located near the bottom outside portion of the link. This lengthens the left and right sides of the parallelogram linkage structure respectively along the brackets 254, 256. The stiffness of the sides of the parallelogram linkage structure along the brackets is proportional to a square of the distance of separation between the pivotal joints 301, 311 and the pivotal joints 302, 312. A bottom side of the housing 601 of the link 292 is made relatively strong to make it stiff and withstand the tension and compression in the link 292 between the pivotal joints 311-312. The upper link 291 provides additional stiffness and strength to withstand the tension and compression in the parallel link 252 through the structure of its housing between the pivotal joints 301-302.

Moreover, a tube may be torsionally stiffened if the ends are not allowed to deform but are maintained in shape, such as a circular shape. Referring back to FIGS. 6A-6B, a small opening 621 in the slanted or diagonally cut end 604 of the housing 601 allows the one or more cables 501 to be routed into the cylindrical cavity 611. To maximize stiffness, the small opening 621 in the slanted or diagonally cut end 604 through which the cables are routed is made as small as possible. In the oval opening at the opposite end 603 of the link 292, a plug 613 is inserted to maintain the cylindrical shape of the cavity 611. The plug has a slit 813 (see FIG. 8) on one side. The slit 813 is forced apart by a screw after installation to expand the plug against the wall or walls of the cavity 611. The plug 613 reduces the size of the oval opening to a smaller opening at the end of the link 292 to increase its torsional stiffness. When the link 292 is finally assembled together, the ends of the cavity 611 are substantially closed with small openings in each to maximize stiffness.

In some applications, the linkage need not be so stiff or support heavy loads such that a serial linkage structure may be employed instead of a parallelogram linkage structure. In which case, a first link may have one end directly coupled to a ground or indirectly coupled to ground and an opposite end pivotally coupled to a second link, the counter balancing link.

The spring assembly 602 includes the spring 515 and a cable clamping mechanism 615. The cable clamping mechanism may also be referred to as a spring piston. The spring 515 is mounted against a flange 614 of the housing 601 at one end and coupled to the one or more cables 501 at an opposite end by the cable clamping mechanism 615. The cable clamping mechanism 615 may include a clamping sleeve 612 and one or more cable end tensioners 616. These and other elements of the cable claming mechanism 615 are described further below with reference to FIGS. 8-13.

The pulleys 502-504 are in substantial alignment together in a plane such that their center points or center point positions are corners of a triangle. The relative positions of pulleys 503 and 504 to each other do not change when the link 292 and the linkage structure moves, such as illustrated by FIGS. 6A-6B. The relative positions of pulleys 502, 504 and the post 505 to each other do not change when the link 292 moves. Thus, two sides of the triangle (the side between pulleys 503-504 and the side between pulleys 504-505) formed by the pivot points of the pulleys 502-504 do not change in length. However, the positions of the pulley 502 and the post 505 do change with respect to pulley 503. Thus, the side of the triangle between pulleys 502 and 503 changes length as the link 292 and linkage structure are moved. That is the triangle formed by the pivot points of the pulleys 502-504 is adjustable in response to movement of the counter balancing link 292. In a horizontal position of the counter balance link and the parallelogram linkage structure, such as illustrated in FIG. 6B, the adjustable triangle formed by the pivot points of the pulleys 502-504 may form a right triangle with at least one corner angle between the sides substantially being a ninety degree angle.

Consider for example, a linear distance X1 between pulleys 502 and 503 when the link 292 is angled upward as illustrated in FIG. 6A. The linear distance between the pulleys 502-503 increases to distance X2 when the link 292 is horizontal, as illustrated in FIG. 6B. A wrap angle of the cable 501 around individual pulleys 502-504 may change as well. However, the sum total wrap angle around the pulleys may remain constant as ends of the cable don't change angle relative to each other. The wrap angle is the angle around the pulley to which the cable makes contact. The wrap angle may also be viewed as the arctuate distance that a segment of the cable contacts the pulley. For example, the wrap angle of the cable 501 making contact to the pulley 504 is a first angle $\theta_1$ when the link 292 is angled upward as illustrated in FIG. 6A. In FIG. 6B, the wrap angle of the cable 501 making contact to the pulley 504 decreases to a second angle $\theta_2$ when the link 292 is horizontal as illustrated in FIG. 6B. Thus, as the post 505 moves with respect to the pulley 503 from its position in FIG. 6A to that of its position in FIG. 6B, some of the cable 501 may be paid out over the pulley 504 to compensate slightly for the increase in the distance between pulleys 502 and 503. Moreover, the wrap angle of the cable 501 around pulley 502 increases from its initial position in FIG. 6A to that of FIG. 6B, and the wrap around pulley 503 increases also, so that the total wrap angle around all of the pulleys 502-504 is conserved. As the total wrap angle around all of the pulleys remains the same, a cable path length PL changes by the same amount as the difference between the linear distances X2 and X1. That is, the change in cable path length, delta(PL), can be determined by the following equation:

$$\mathrm{delta}(PL)=X2-X1$$

A change in the cable path length around the pulleys results in a change in tension in the spring 515 and the one or more cables 501. For a given weight at the joint 250, a greater moment at axis 311 is applied to the link 292 when the link is in the horizontal position as illustrated in FIG. 6B than when the link 292 is in the upward angled position as illustrated in FIG. 6A. This is due to different moment arm lengths in the different positions of the counter balancing link and the different deformations of the parallelogram linkage structure. Assuming the total cable length remains constant (e.g., there is no stretch or slippage in the clamps), as the distance X2 between the pulleys 502-503 becomes greater than X1, the cable 501 is pulled on and out from the link 292 to additionally compress the spring 515 and compensate for the greater moment being applied at the axis 311. If the link 292 is moved further downward (not shown) past the horizontal position that is illustrated in FIG. 6B, an additional length of cable is pulled out from the link 292 to further compress the spring 515 and further increase the tension therein. As the link goes below horizontal, the triangle formed by the pulleys becomes obtuse and there is a loss in mechanical advantage for the spring. The loss in mechanical advantage is compensated for by the increased compression. As the link 292 moves back to its upward angled position, such as illustrated in FIG. 6A, the cable 501 is released back into the link 292 so that the spring 515 is decompressed and the tension is reduced in the spring 515 and cable 501 to compensate for a lower level of moment being applied at the axis 311. In this manner after the initial tensions are set, the link 292 can properly counter balance a weight at differing positions with respect to the bracket 254 and the joint 248.

FIGS. 5 and 6A-6B illustrate one embodiment of a counter balance link 292 and idle link 291 in a set-up arm. However, the counter balance link 292 and idle link 291 in the set-up arm may be further compacted trading off the amount of motion. For example, the counter balance link 292 may move positive and negative forty degrees from the horizontal position illustrated in FIG. 6B. If less motion is acceptable, the counter balance link may be further compacted.

Figure 7:
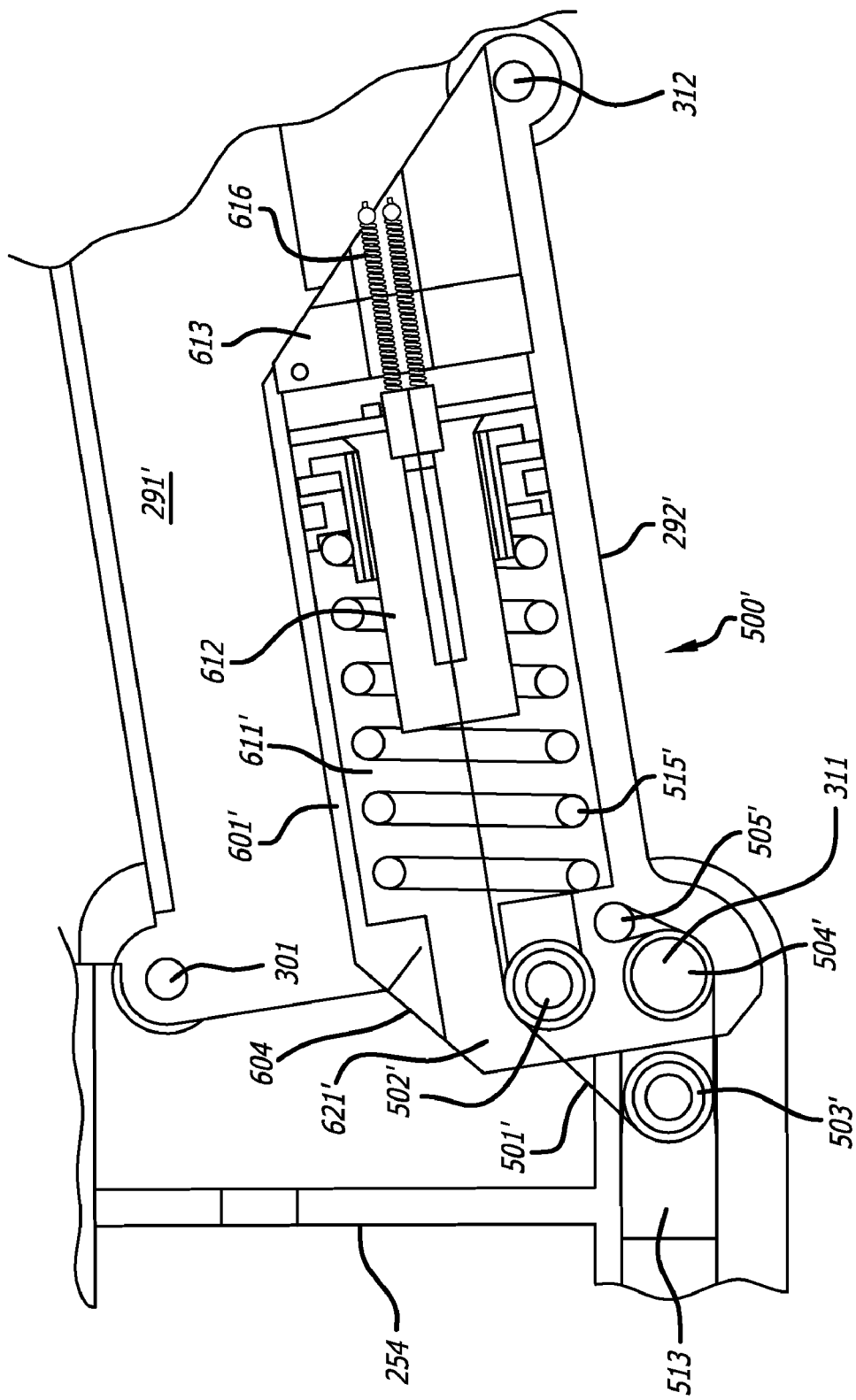
FIG. 7 is a right side cutaway view of second set-up arm with a compact counter balance mechanism.

Referring now to FIG. 7, an embodiment of a more compact counter balance link 292' in a set-up arm is illustrated. An idle link 291' is coupled in parallel to the counter balancing link 292'. The counter balance link 292' may move positive and negative thirty degrees from a horizontal position, such as that illustrated by link 292 in FIG. 6B Referring now to FIGS. 6A-6B and 7, the link 292' is somewhat similar to link 292 including similar elements with slight differences. For example, the link 292' includes pulleys 502'-504' and post 505' similar to pulleys 502-504 and post 505 in link 292. However the positions of the pulleys 502',504' and post 505' differ somewhat from the position of pulleys 502,504 and post 505. The one or more cables 501' in the link 292' are shorter than cables 501 in link 292 given the lesser degree of motion. The hollow housing 601' of the link 292' is shorter than the hollow housing 601 of the link 292. An opening 621' into the cylindrical cavity 611' of the housing 601' differs somewhat from the opening 621 into the cylindrical cavity 611 of the housing 601. The spring 515' in the link 292' is shorter than the spring 515 in the link 292. But for these differences, the elements of link 292' function similar to the elements of link 292.

Referring now to FIG. 8, a perspective view of the compact counter balance link 292 separate from the parallelogram linkage structure 246 is illustrated. At the slanted or diagonally cut end 603 of the housing 601, the plug 613 closes the cavity 611 in the housing 601. One or more cable end tensioners 616 extend out from the plug 613. Near the opposite end of the housing is a shaft 802 extending through the housing with ends coupled to thereto.

Referring now to FIG. 9, a perspective view of the compact counter balance link 292 is illustrated with the hollow housing 601 removed to better show the internal elements. Within the housing 601, the pulley 502 is rotatably coupled to the shaft 802. Within the housing 601 at the pivotal joint 311, the pulley 504 is mounted on a shaft 902 between spaced apart pair of bearings 820 mounted on the shaft. The shaft 902 extends through the base of the housing 601 at one end. At the opposite end of the base at the pivotal joint 312, another shaft 903 extends through the base of the housing 601 and has another pair of spaced apart bearings 820 mounted thereto.

The plug 613 has a cylindrical shape to match the cavity and has a flat end at one end and a slanted oval-like shaped end at an opposite end to match the slanted or diagonally cut end 603 of the housing 601. The clamping sleeve 612 of the cable clamping mechanism 615 may be coaxial with the spring 515 in a center opening thereof so that it is substantially surrounded by the spring 515.

Figure 10:
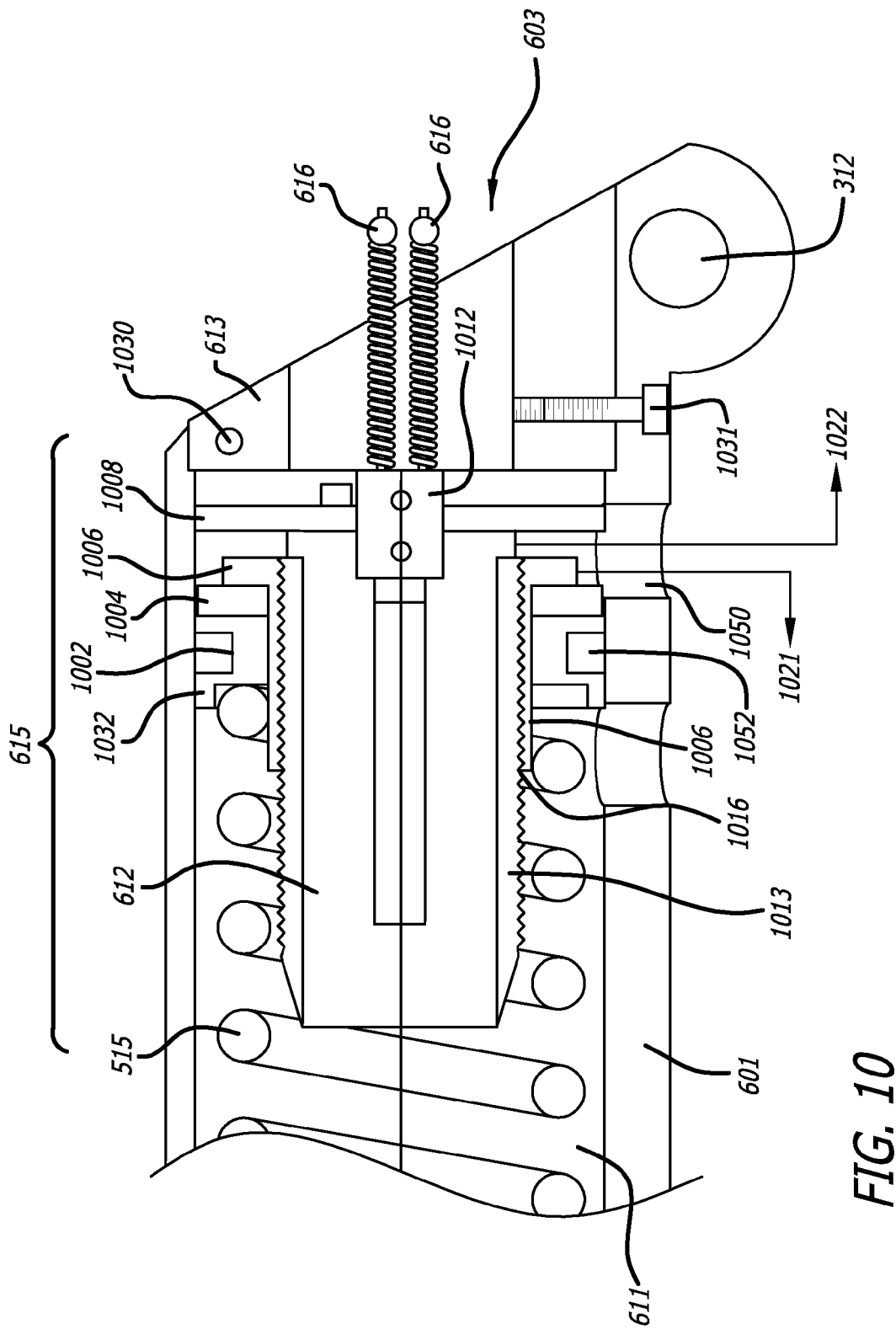
FIG. 10 is a magnified cutaway view of a portion of the compact counter balance link.

Referring now to FIG. 10, a magnified cutaway view of a portion of the compact counter balance link 292 is illustrated.

The cable clamping mechanism 615, also referred to as a spring piston, includes the clamping sleeve 612 (also referred to as a counterbalance tube); a mating ring 1002 (also referred to as a spring flange); a thrust bearing 1004, a preload adjustment nut 1006, and an anti-rotation plate 1008 coupled together as shown.

Referring now to FIGS. 10 and 16A-16C, the plug 613, is inserted into the cavity 611 to plug up the opening in one end of the housing 601. The fastener 1031 is inserted into the threaded hole 1631 to maintain the alignment of the plug 613 in an appropriate position along the cavity wall. A spreading screw 1030 is inserted into a threaded opening 1630 in the split side of the plug 613. A set screw 1632 may be inserted into a threaded opening 1631 to provide a backstop for the spreading screw 1030. Alternatively, the threaded opening 1631 may be filled solid forming part of the split flange. As the end of the spreading screw 1030 aligns and mates with the end of the set screw 1632, the split 813 and the plug 613 begin to expand. With further tightening of the screw 1030, the split 813 expands further forcing the sides of plug tightly against the wall of the cavity 611 to torsionally stiffen the compact counter balance link 292. If the plug 613 is to be removed, the set screw 1632 may be removed and the spreading screw 1030 may be replaced with a special screw that has threads removed near its head, so that it can turn freely on the threads on that side of the split. If the sides of the plug 613 are stuck in expansion against the wall of the cavity, the special screw may be further threaded into the opening 1631 pulling the split side of the plug together and the sides of the plug away from the wall of the cavity. In this manner, the plug should be more readily removed from the cavity 611 for disassembly and maintenance of the counter balance link.

The plug 613 has a center opening 1602 to allow the one or more cable end tensioners 616 to pass through to the clamping block 1012. The one or more cable end tensioners 616 are used to remove slack and pre-tension the one or more cables 501 with substantially equal tension during assembly. The one or more cable end tensioners 616 are better illustrated in FIG. 13.

Figure 13:
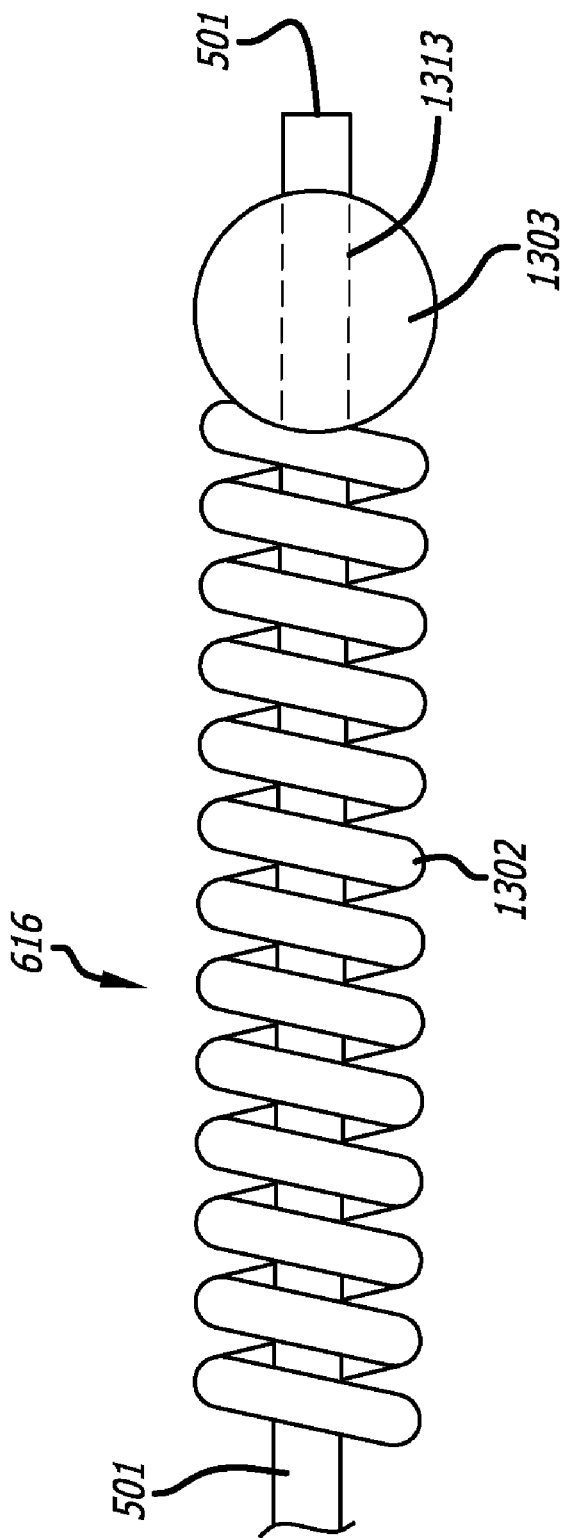
FIG. 13 is a side perspective view of a cable end tensioning mechanism.
Figures 17A, 17B:
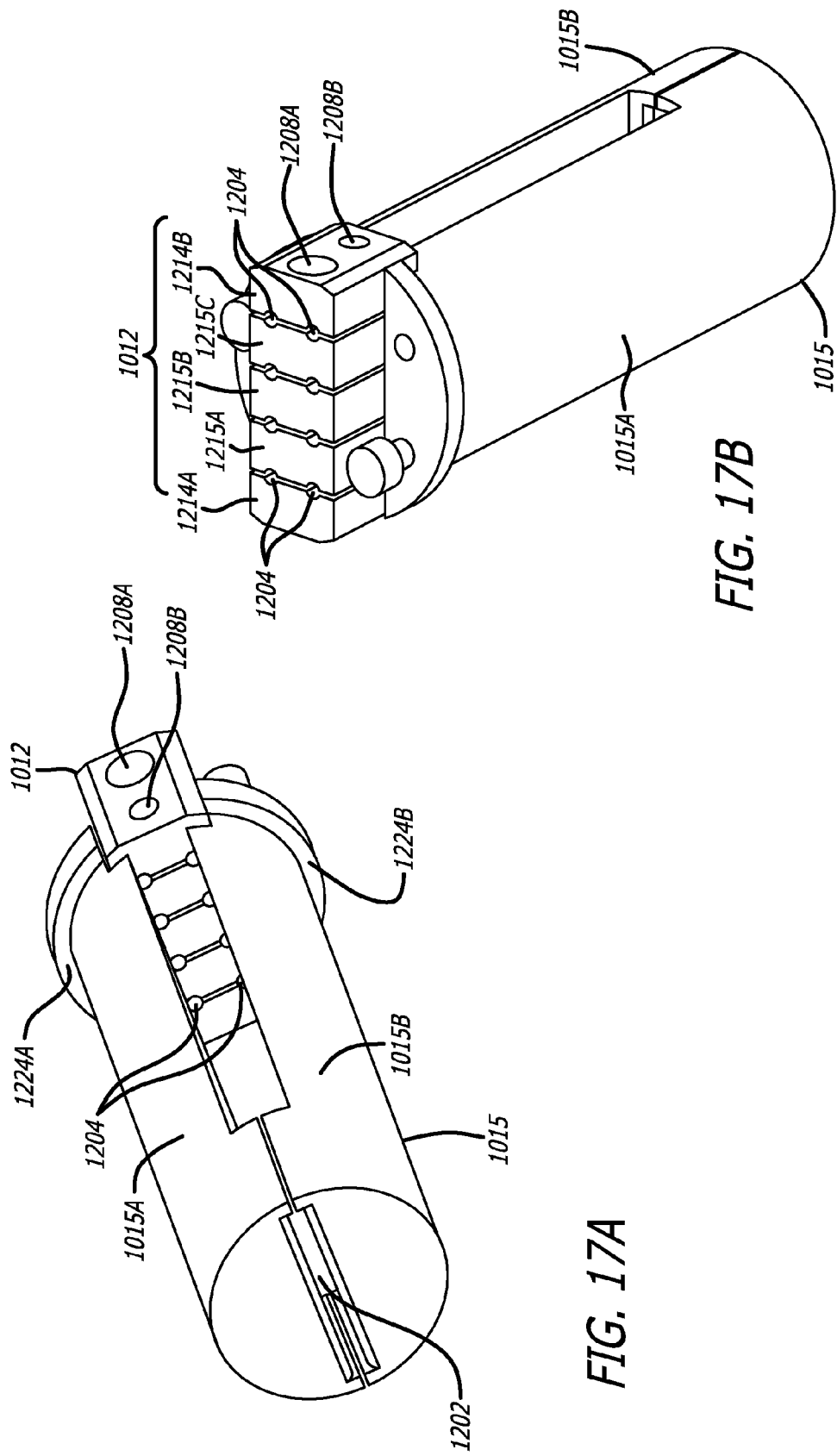
FIGS. 17A-17B are perspective views of an assembled ribbonizer and clamping block illustrated in exploded views of FIGS. 12A-12B.

Referring momentarily to FIG. 13, each of the one or more cable end tensioners 616 includes a pre-tensioning spring 1302 and a cable terminator 1303. The cable terminator 1303 may be a ball, a sphere, a tube, a cylinder, or other block shape. The cable terminator 1303 has a cylindrical opening 1313 to slide over the end of the cable 501. The cable terminator 1303 may be crimped to an end to the cable 501 to retain the spring 1302 on the cable. The pre-tensioning spring 1302 is trapped between the clamping block 1012 of the clamping sleeve 612 on one side and the cable terminator 1303 on the opposite side. The pre-tensioning springs 1302 pull out on the one or more cables 501 to pretension the cables prior to clamping the clamping block 1012 thereto.

Referring now back to FIG. 10 and to FIGS. 12A-12B and FIGS. 17A-17B, the clamping mechanism 615 includes the threaded counter balance sleeve 612, the clamping block 1012, the mating ring 1002, the thrust bearing 1004, the ribbonizer 1015, the threaded nut 1006, and the alignment plate 1008. The one or more cables 501 are routed through the spring 515, the ring 1002, the bearing 1004, the threaded sleeve 612, the ribbonizer 1015, and the nut 1006 into and through openings 1204 of the clamping block 1012 and an opening 1120 in the alignment plate 1008.

The ribbonizer 1015 is formed of two ribbonizer halves 1015A-1015B. Each half 1015A-1015B has a planar portion 1202A-1202B, respectively, that are spaced apart to planarize and substantially align the one or more cables 501 for routing over the pulley 502. When the halves are coupled together, the planar portions 1202A-1202B in each leave an opening 1202 into the ribbonizer 1015. The two ribbonizer halves 1015A-1015B include a slot 1212A-1212B respectively to receive the clamping block 1012. During assembly, the two ribbonizer halves 1015A-1015B are inserted into and fit tightly within the threaded sleeve 612. The ribbonizer halves further include a ridge segment 1224A-1224B to mate with a circular edge of the threaded sleeve 612, acting as a stop so that the ribbonizer does not move further down into the threaded sleeve. The clamping block 1012 doesn't move relative to threaded sleeve 612 or the ribbonizer 1015.

The clamping block 1012 may be formed of five clamping plates 1214A-1214B, 1215A-1215C stacked over each other together to clamp to the one or more cables 501. The five clamping plates 1214A-1214B, 1215A-1215C capture the one or more cables 501 in grooves 1204A-1204B between each. Each of the interior clamping plates 1215A-1215C may include a pair of grooves 1204A on one side and a pair of grooves 1204B on the opposite side and a pair of holes 1221 to allow the clamping screws 1028A-1208B to slide through. The outer clamping plate 1214A may include the pair of grooves 1204B in a bottom side while the outer clamping plate 1214B includes the pair of grooves 1204A in a top side. The grooves 1204A-1204B are a little shallower than half the diameter of a cable 501. In one embodiment of the invention, the diameter of each of the one or more cables 501 is 0.062 inches. The clamping plates are stacked next to each other, with a cable segment or cable 501 in each groove, nestled partway into the groove in a plate on one side, and in the groove of another plate on the other side. The parallel pair of grooves 1204A-1204B in the clamping plates respectively align up together with the parallel pair of grooves 1204B-1204A of another clamping plate forming the openings 1204 in the clamping block 1012 to clamp around the cable or cable segments.

The outer clamping plate 1214A further includes a threaded opening 1220 to receive the threads of the clamping screw 1208A and a through opening 1221 to allow the clamping screw 1208B to pass through it into the other clamping plates. The outer clamping plate 1214B further includes a threaded opening 1220 to receive the threads of the clamping screw 1208B and a through opening 1221 to allow the clamping screw 1208A to pass through it into the other clamping plates. Thus, the outer clamping plates 1214A-1214B may be substantially similar to reduce cost. In this manner, the clamping screws 1208A-1208B squeeze all clamping plates together from opposite sides to conserver space and assemble the clamping block 1012 together. The screw clamping force is not divided up between the joints of the clamping plates, but rather is applied to all. Thus, the clamping screws 1208A-1208B may be small screws and can still clamp with a substantial clamping force around the cables.

In one embodiment of the invention, with five clamping plates and four joints between them each having a pair of grooves between them, eight cables or eight cable segments of four cables may be received. With additional clamping plates more cables or cable segments may be received. Alternatively, additional grooves may be provided in each to increase the number of cables or cable segments clamped by the clamping block 1012. Alternatively, fewer grooves may be provided in each to increase the clamping force. In one embodiment of the invention, the clamping plates may only have one groove instead of a pair of grooves per side to provide twice the clamping force. To clamp around eight cables or eight cable segments of four cables, nine clamping plates are provided, two outer clamping plates 1214A-1214B and seven interior clamping plates.

As previously mentioned, the two ribbonizer halves 1015A-1015B include a slot 1212A-1212B respectively so that the ribbonizer 1015 may receive the clamping block 1012. The threaded sleeve 612 also includes a pair of slots 1213 on opposite sides to receive a portion of the clamping block 1012 and hold it in place. The clamping block 1012 is in turn fitted into the opening 1120 in the anti-rotation plate 1008 to keep the clamping block 1012, the threaded sleeve 612, and the ribbonizer 1015 from rotating in the cavity 611 of the housing 601.

An end of the ribbonizer 1015 is bolted to the anti-rotation plate 1008. At least one pair of fasteners 1122 are inserted through at least one pair of diagonally spaced apart holes 1121 in the anti-rotation plate 1008. The pair of fasteners 1122 are threaded into at least one pair of threaded holes 1241 to couple the ribbonizer to the anti-rotation plate.

The threaded sleeve 612 has an external thread 1013 to threadingly engage an inner thread 1056 of the nut 1006. The tension adjustment in the one or more cables 501 is provided by rotating the nut 1006 onto the threaded sleeve 612 to compress the compressible spring 515. The internal threads 1056 of the nut 1006 match the outer threads 1013 of the threaded sleeve 612.

Each end of the one or more cables 501 has a cable terminator 1303 crimped near its end and a spring 1302. The spring 1302 is trapped between the cable terminator 1303 and the end of the clamping block 1012. If there were no springs 1302, it would be difficult to make the tensions the same in the one or more cables 501, because the cables are not manufactured exactly the same length, and they may stretch varying amounts during initial assembly. During assembly, the clamping plates of the clamping block 1012 are initially left loose. The compression on the compression spring 515 and the tension in the one or more cables is partially adjusted for the expected weight. The spring assembly 602 including the clamping mechanism 615 is run back and forth in the housing 601 by pivoting the link 292 to take out the initial stretch. At this point, all the tension on each cable is being applied to the springs 1302. Due to the variations previously mentioned above, some of the springs 1302 may be compressed more than others. The difference in tension between the one or more cables 501 or their segments is the difference in length times the spring rate of the springs 1302. For example, if the difference in length between a pair of segments or cables is 0.06 inches and the spring rate is 52 pounds/inch, the difference in tension is 3 pounds (lb). The difference in tension in other cables or cable segments may be within a range of ten pounds, such as 8 lb or 5 lb for example.

After the one or more cables are pre-tensioned, the clamp screws 1208A-1208B are tightened to clamp the one or more clamping plates of the clamping block around the one or more cables 501. Then the compact counter balancing mechanism can be adjusted for proper balance by compression adjustment in the compression spring and adjusting the dimensions of the triangle formed by the center points of the pulleys. Prior to further adjustment, the total load in the spring 515 is about 500 lb, and if eight cable segments are used, about 500/8 or 62lb per cable segment. As long as each of the one or more cables 501 have the same characteristics, the difference in tension between the cable segments or cables remains. For example, some of the segments or cables will have a tension of 60 lb while other will have a tension of 63 lb. The percentage variation in tension is relatively small, and each of the cable segments or cables share the load well. Another function of the springs 1302 and cable terminators 1303 of the cable end tensioners 616 is that if the clamp plates of the clamping block 1012 were to slip, the cables 501 could only slide a little bit until the springs 1302 went to their solid height. The cable terminators 1303 of the cable end tensioners 616 are crimped sufficiently to the ends of the one or more cables so they will not give with the maximum load being applied to the spring 515.

The preload balance adjustment nut 1006 extends along a portion of the threaded sleeve 612 and includes an internal thread 1016 to threadingly engage the external thread 1013 of the threaded sleeve 612. As the nut 1006 is turned in one direction, it pulls out on the threaded sleeve 612 and compresses the spring 515 through the mating ring 1002 and the thrust bearing 1002. The arrows 1021-1022 in FIG. 10 illustrate the direction of movement of the nut 1006 along the sleeve 612 as the nut is turned to generate a larger tension in the spring 515 and the one or more cables 501. The coaxial threaded sleeve 612 and its cable clamp 1012 are moved outward away from the spring 515 to increase the tension in the spring 515 and the one or more cables 501. The nut 1006 is turned in an opposite direction so that the threaded sleeve 612 and its cable clamp 1012 move into the spring 515 thereby releasing tension in the spring 515 and the one or more cables 501. In a bottom side of the housing 601 are one or more openings 1050 into the cavity 611 to gain access to and adjust the nut 1006.

Due to friction, the nut 1006 can't be adjusted when the full force of the spring 515 is pushing on it. There are pin holes 815 in the each side of the housing 601 into which spring holding pins may be inserted. To pin the spring 515, the counter balancing mechanism is pulled up or down until an appropriate pair of pin holes 815 on each side of the housing line up with the groove 1052 in the mating ring 1002 and put a restraining pin (not shown) in from each side to restrain the spring 515 from releasing. Lifting up on the counter balance link 292 relieves the tension force from the cables so that the adjustment nut 1006 can be turned easily. After the adjustment nut 1006 is rotated an appropriate amount, the restraining pins are removed from the groove 1052 and the pin holes 815 so that the spring 515 releases back into a position along the cavity 611 to apply a tension in the one or more cables 501.

The mating ring 1002 mates the spring 515 to the clamping mechanism. The mating ring 1002 includes an aligning lip 1032 on one side. The aligning lip 1032, along with the body of the threaded sleeve 612, hold the spring 515 in alignment at one end within the cavity 611 of the housing 601. An opposite side of the mating ring 1002 couples to the thrust bearing 1004.

On one side, the thrust bearing 1004 allows the nut 1006 to rotate so that its threads 1016 can threadingly engage the threads 1013 of the threaded sleeve 612. The opposite side of the thrust bearing 1004 presses down against a side of the mating ring 1002 to compress the spring 515.

Figure 11A:
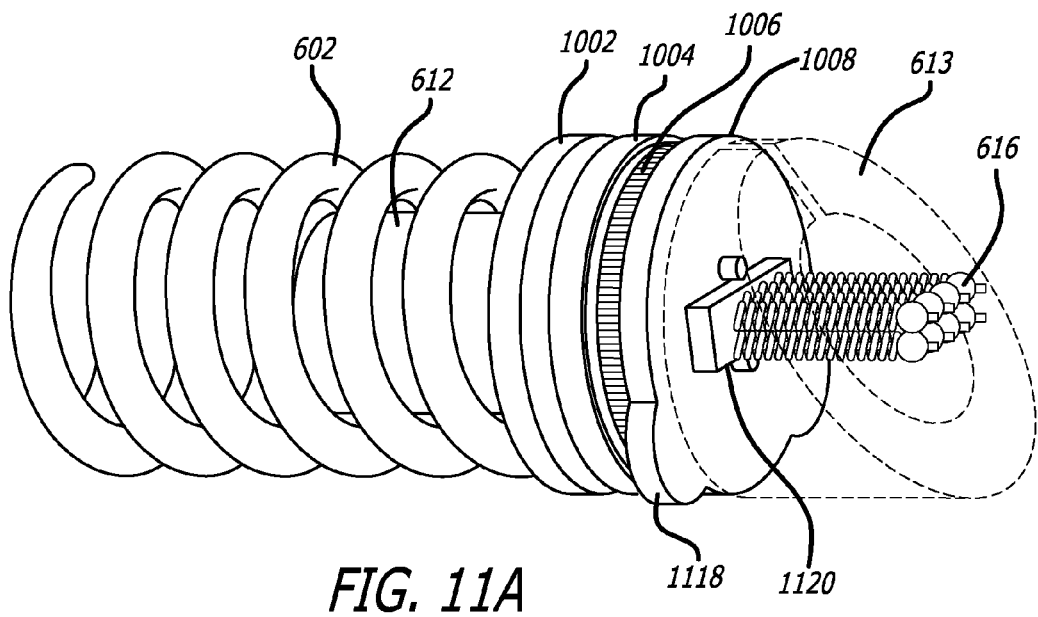
FIGS. 11A-11B are perspective views of the compact counter balance link with removed elements.
Figure 11B:
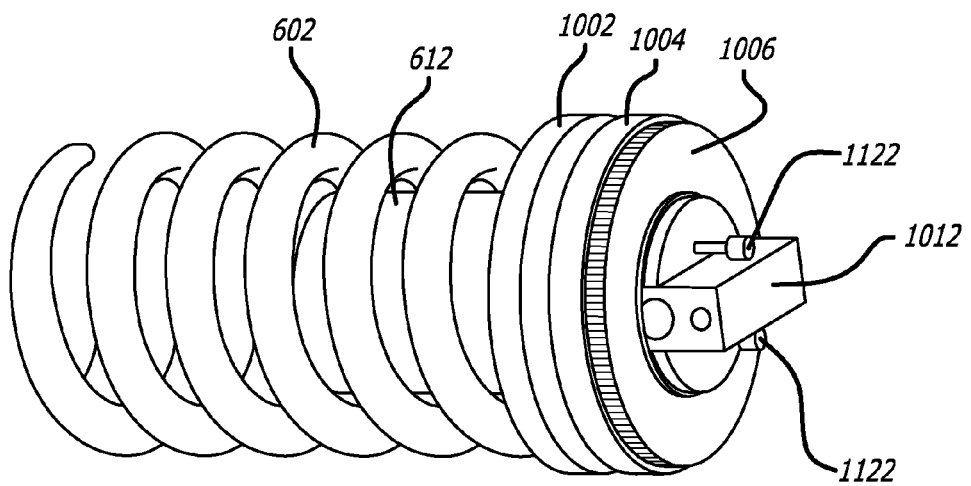
Figure 12A:
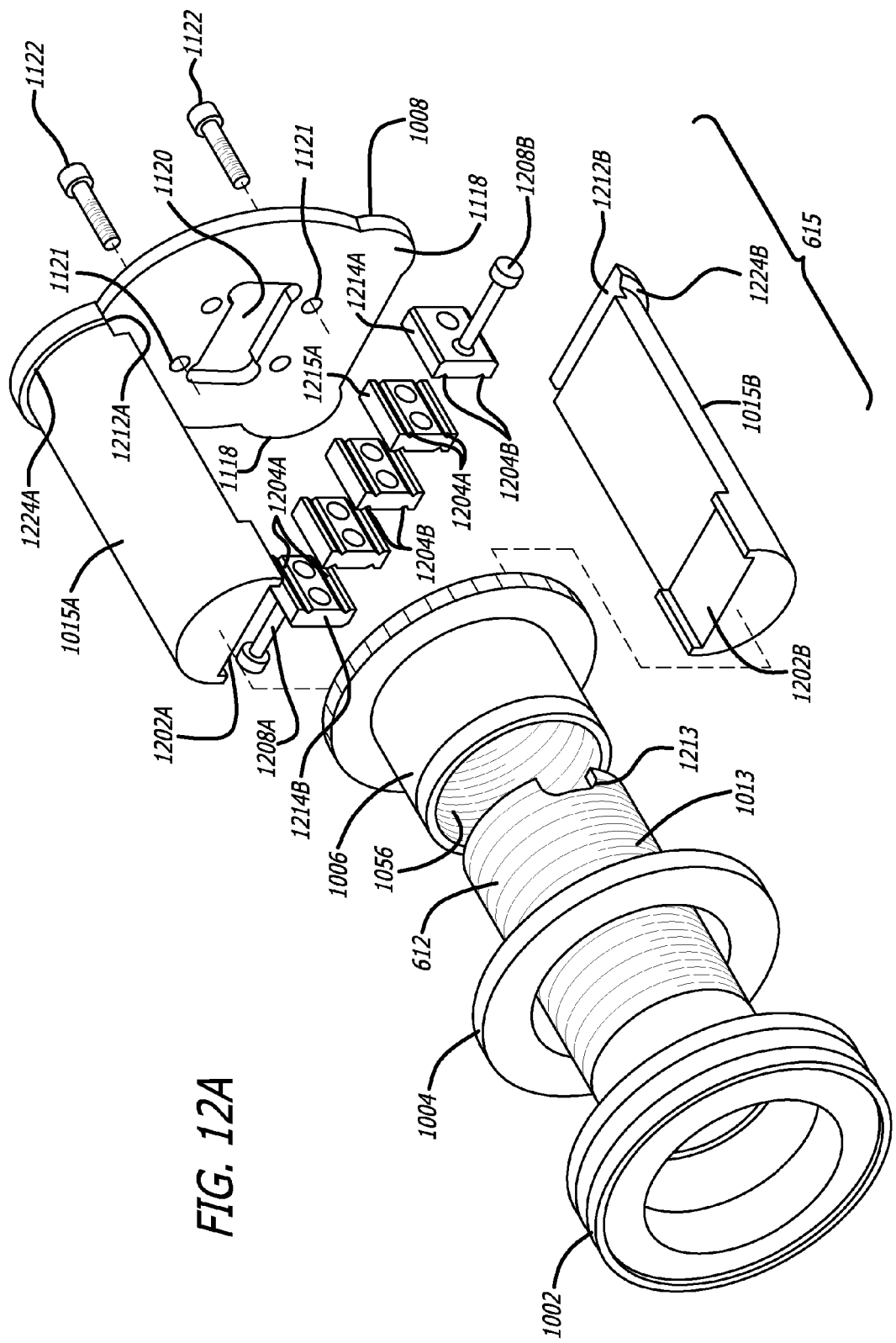
FIGS. 12A-12B are exploded perspective views of the clamping mechanism.
Figure 12B:
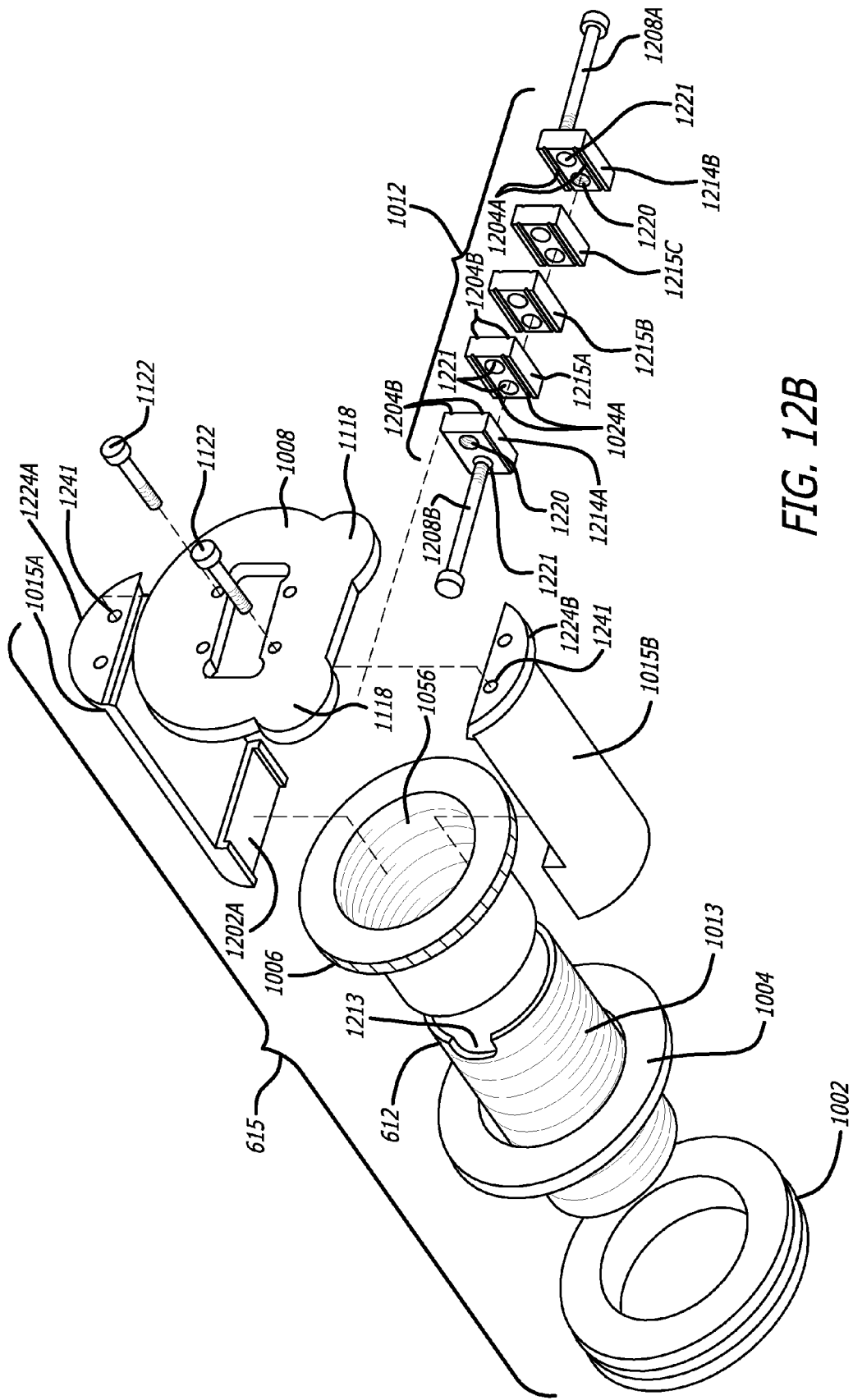

Referring now to FIGS. 10 and 11A-11B, the anti-rotation plate 1008 has one or more protrusions 1118 (see FIG. 11A) that engage recesses (not shown) within the cavity 611 of the housing 601. A rectangular opening 1120 in the anti-rotation plate 1008 receives the clamping block 1012. One or more bolts or fasteners 1122 couple the anti-rotation plate 1008 to the top of the threaded sleeve 612. The one or more protrusions 1118 of the anti-rotation plate 1008 when engaged into the recesses of the cavity in the housing deter the threaded sleeve 612 and the clamping block 1012 from rotating within the cavity 611 as the pre-tensioning nut is turned. This allows the pre-tensioning nut to adjust the tension and avoids the one or more cables 501 from twisting together. With the protrusions 1118 in the recesses, the anti-rotation plate 1008 moves along the wall of the cavity 611 with the threaded sleeve 612 as the nut 1006 is turned and as the spring is compressed and released by the one or more cables 501.

As shown in FIGS. 8-9, the plug 613 may include a split 813 along a top portion to split it into split portions and allow the end cap to slightly compress when inserted into the cavity 611 of the housing 601. As is illustrated in FIG. 10, the plug 613 includes a fastener 1030 near its top portion having the split 813. The fastener 1030 forces the split portions of the plug 613 apart to expand the plug 613 against the walls of the cavity 611. A fastener 1031 is inserted through the housing 601 and threaded into a bottom portion of the plug 613. The fastener 1031 aligns the plug 613 within the cavity 611. One end of the springs of the cable end tensioners 616 couples to the clamping block 1012. The opposite end of the springs couple to a cable terminator that is crimped onto each of the one or more cables.

To couple the cable clamping mechanism to the one or more cables near their ends during assembly of the parallel linkage structure 246 and the counter balancing link 292, the compression spring 515 is pinned into a compressible state by inserting a pair of pins into one of the holes 815 on each side of the housing 601 so that the nut 1006 may be turned. From the post 505, the one or more cables 501 are routed over the pulleys 502-504 or 502'-504' and into the cavity 611,611' and through the spring 515. The one or more cables are further slid through the clamping plates of the clamping block 1012. Each of the one or more cables 501 is independently pre-tensioned by the one or more cable end tensioners 616 to remove the slack in the cables and to substantially equalize an initial tension in each. In one embodiment of the invention, the initial tension in each cable is set by the spring 1302 in the cable end tensioner 616. In one embodiment of the invention, the initial tension in each cable is on the order of ten pounds.

After pre-tensioning the one or more cables 501, the clamping mechanism is engaged to clamp the one or more cables to the clamping block 1012. The clamping screws are turned to move the clamping plates to capture the one or more cables against the clamping block 1012.

Next, the one or more cables 501 are tensioned to counter balance an expected weight or load that is to be supported at the set-up arm. The load may be the weight of a robotic arm, medical equipment, further linkage or other devices that may couple to the parallelogram linkage structure. The pre-load adjustment nut 1006 is turned to adjust the tension in the spring 515 and establish a tension in the cables. The tension in the spring 515 may be substantially equally shared by the one or more cables 501. The position of block 513 to which the pulley 503 is coupled may also be adjusted as needed to compensate for spring variations or load variations.

With the counter-balancing link assembled and calibrated in the parallelogram linkage structure, the expected weight or load on the set up arm can be balanced out so that the linkage structure can be readily moved in a vertical direction against the force of gravity. As the linkage structure is moved, the moment or force at the joints of the counter-balancing link may vary. The counter-balancing link 292 balances out or compensates for the variance or change in moment or force at its joints. Generally, the variable force or moment generated by the counter-balancing link 292 to balance out or compensate for the moment or force at its joints may be referred to as a counter balancing force or counter balancing moment. The one or more cables 501 wrap or unwrap over the pulleys 502-504 in the counter balancing link 292 to compress or decompress the spring 515 and respectively increase or decrease the tension in the one or more cables 501 in generating the counter balancing force. An increase in tension in the one or more cables 501 balances out an increase in moment or force at the joints of the counter balancing link 292. A decrease in tension in the one or more cables 501 balances out a decrease in moment or force at the joints of the counter balancing link 292.

After the set-up arm has been moved into proper position and the load or weight balanced out, the set-up joint brakes may be applied to deter movement in the set up arm, the parallelogram linkage structure, and the counter balancing link 292.

Compact Spring Balancing Theory

Referring now to FIG. 14A, a single link 1400 is illustrated pivotally coupled to a vertical wall 1402 at a pivot point O. The link 1400 rotating in a vertical (and horizontal) plane can be balanced by a linear spring 1401 so that it is in equilibrium in any position despite the effect of gravity. The force of gravity (f=mg) is equal to the mass m times the acceleration of gravity g which is exerted at the midpoint of the link. The length of the link 1401 is 2l so that its midpoint is a distance l along the link. The linear spring 1401 has a spring constant K and couples to the link 1401 at a point v and the wall 1402 at a point w. The link 1400 makes an angle theta with the wall W as illustrated in FIG. 14A.

Referring now to FIG. 14B, a schematic diagram of the rigid link 1400 is illustrated pinned at point O and held by the linear spring 1401 attached to the vertical wall 1402 at the point w. A distance x separates points w and v. A distance b separates points w and o. A distance a separates points o and v. A distance t is along a line between point o and a point normal to the line between points w and v.

For the link to be in equilibrium with the force of gravity, the moment $M_o$ about the point O should be substantially zero. From FIG. 14B we can determine the equation for the moment $M_o$ about the point O as:

$$M_o = mgl \sin \theta - K(x-x_o)t = 0$$

where $x_0$ is the unstretched length of the spring.
Rearranging the terms of the equation we have $$mgl \sin \theta = K(x-x_o)t$$

With the link 1400 at an angle theta (θ) with the wall that is not equal to zero, we can substitute in an equation for t derived from similar triangles (see FIG. 15B):

$$t/b = a \sin \theta / x$$

Rearranging the equation to solve for t we find:

$$t = ab \sin \theta / x$$

Substituting in the equation for t which cancels the sine terms we find:

$$mgl = K(x-x_o)ab/x$$

If the unstretched length of the spring, $x_0$, is equal to zero, the equation further reduces to:

$$mgl = Kab$$

Rearranging the terms to solve for the spring constant, we have:

$$K = mgl/ab$$

Thus, the equation for the spring constant K indicates that the stiffness K of the spring 1401 can be constant and independent of the angle theta θ of the link. The stiffness K of the spring can be constant and independent of the angle theta θ if the unstretched length $x_0$ of the spring 1401 is chosen to be substantially zero. The unstretched length $x_0$ of the spring 1401 may be set to substantially zero if the tension spring 1401 is placed outside the line connecting the points w and v.

Therefore, the link 1400 may be balanced for all of its positions if (i) the stiffness K of the spring is properly chosen according to the equation K=mgl/ab; and (ii) the spring is placed outside of the line wv between its connection to the link and a fixed reference point.

Referring now to FIG. 15A, a spring, pulley, and cable counter balancing mechanism for the link 1400 is illustrated. FIG. 15A illustrates a tension spring 1501 placed outside the line connecting points w and v so that the unstretched length $x_0$ of the spring 1501 is effectively set to substantially zero. A cable 1503 is routed from the spring 1501 over a pulley 1502 at the point v and coupled to the wall 1402 at the point w. For accurate balance, the diameter of the pulley 1502 should be small relative to the sides a and b of the triangle. However where spring loads are high, a cable that is strong enough to hold a load safely needs a pulley of an appropriate size so as not to fail from bending fatigue during use. Thus, the single pulley 1502 may not be practical for some applications. In which case, a three pulley system may be used as illustrated in FIG. 15C.

FIG. 15B illustrates a schematic diagram of the rigid link 1400 with a similar triangle to that of FIG. 14A. FIG. 15C illustrates a schematic diagram of a three pulley system corresponding to the schematic diagram of FIG. 15B. As described previously, the distance x separates points w and v. The distance b separates points w and o. The distance a separates points o and v. The distance t is along a line between point o and a point normal to the line between points w and v.

In FIG. 15C, a schematic diagram of a spring-cable-pulley balancing mechanism is illustrated with three pulleys 1512A-1512C for balancing the weight and moment of the link 1400. A cable 1513 is wrapped around a portion of each of the three pulleys 1512A-1512C. Each of the three pulleys 1512A-1512 may be of equal diameter, and the distances a and b in the system can be maintained constant. However as the angle theta θ changes, the total cable path length (a+b+x) of the cable 1513 changes by the same amount as x does, because the total wrap angle of the cable 1513 on the three pulleys is constant. The change in cable length pulls or pushes on the spring of the spring assembly 602 and adjusts the counter balance force applied to maintain a substantially zero moment and balance out the weight of the link.

The additional weight of additional links and an attached robotic surgical arm may also be balanced out by a counter balancing force with an appropriate choice of spring constant K and cabling that is capable of withstanding the additional forces applied.

CONCLUSION

While a parallelogram link structure 246 of the set-up joint arm 140 has been described in detail with reference to the patient side manipulator (PSM) 132, a parallelogram linkage structure may be also used in the set-up joint center arm 138 supporting the endoscope camera robotic manipulator 134 or other set-up joint arms or structures of a robotic surgical system.

As illustrated in FIG. 1, the set-up joint center arm 138 comprises a relatively short, near vertical rigid arm defined primarily by the parallelogram link structure 246. The set-up joint center arm 138 has a shorter parallelogram link 252 than the other three arms 140, 142, 144. The set-up joint center arm 138 has three degrees of freedom that are typically manually positioned. The set-up joint center arm 138 is free of any redundant joints as the azimuth angle is controlled by the rotation of the orienting platform 136. The set-up joint center arm 138 may be vertically translated similar as denoted by arrow SJC3. The general rotational motion of the set-up joint center arm 138 is denoted by arrow SJC4 in FIG. 1.

While embodiments of the invention have been described in detail with reference to a ceiling mounted robotic surgical system 100, the embodiments of the invention may be equally applicable to robotic surgical systems that do not mount to the ceiling but instead are supported by flooring or mounted to a table. Additionally, the embodiments of the invention have been described in detail with reference to a parallelogram linkage structure. However, the embodiments of the invention may be equally applicable to other linkages, such as serial linkage arm structures that are to be counter balanced or other parallel linkage structures that are to be counter balanced. Moreover, the embodiments of the invention have been described with reference to a spring-cable-pulley counter-balancing mechanism. The cable and pulleys may instead be a belt or strap and pulleys, a chain and sprockets, a perforated metal tape and pulleys with bull nose pins, or a timing belt and timing gears. The pulleys, sprockets, pulleys with bull nose pins and timing gears may be collectively referred to as rotating transmission devices. The cable, belt, strap, chain, perforated metal tape, and timing belt may be collectively referred to as a tension mechanism.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A set-up arm to support a robotic arm, the set-up arm comprising:
   a first set-up joint to couple to a support structure;
   a second set-up joint spaced apart from the first set-up joint, the second set-up joint to couple to a robotic arm to provide support thereto;
   a counter balancing link pivotally coupled to the first set-up joint at a first pivot point and to the second set-up joint at a second pivot point, the counter balancing link to balance out the force of load at the second set-up joint, the counter balancing link including a hollow housing having a cylindrical cavity with a first opening at a first end;
   a spring in the cylindrical cavity having a first end coupled to the hollow housing, the spring to provide a spring force to balance out the force of load at the second set-up joint;
   a plurality of pulleys including a first pulley rotatably coupled to the first set-up joint at the first pivot point between the counter balancing link and the first set-up joint, and one of a pair of pulleys rotatably coupled to the first setup joint and another one of the pair of pulleys rotatably coupled to the hollow housing;
   at least one cable under tension coupled to the setup arm and wrapped over the plurality of pulleys to couple to a second end of the spring; and
   wherein a linear distance between the pair of pulleys varies to change a cable path length in response to the pivoting of the counter balancing link with respect to the first set-up joint to modify the spring force and the tension in the at least one cable under tension to counter balance changes in moment and mechanical advantage.

2. A set-up arm to support a robotic arm, the set-up arm comprising:
   a first set-up joint to couple to a support structure, the first set-up joint having a first pulley rotatably coupled thereto;
   a second set-up joint spaced apart from the first set-up joint, the second set-up joint to couple to a robotic arm to provide support thereto;
   a counter balancing link pivotally coupled to the first set-up joint at a first pivot point and to the second set-up joint at a second pivot point, the counter balancing link to balance out the force of load at the second set-up joint, the counter balancing link including
       a hollow housing having a cylindrical cavity with a first opening at a first end
       a second pulley rotatably coupled to the hollow housing,
       a first compression spring in the cylindrical cavity having a first end coupled to the housing, the first compression spring under compression to balance out the force of load at the second set-up joint; and
       a third pulley having a center point at the first pivot point between the counter balancing link and the first set-up joint, wherein center point positions of the first, second, and third pulleys are corners of a triangle, wherein the triangle formed by the center point positions of the first, second and third pulleys is adjustable in response to pivoting of the counter balancing link with respect to the first set-up joint to modify the tension in the at least one cable under tension;
   at least one cable under tension wrapped over the second pulley into the cylindrical cavity and coupled to a second end of the first compression spring, the at least one cable under tension further wrapped over the first and third pulleys and coupled to the set-up arm;

and wherein
a sum of the wrap angles of the at least one cable under tension wrapped around the first, second and third pulleys is substantially constant in response to the pivoting of the counter balancing link with respect to the first set-up joint; and
a linear distance between the first pulley and the second pulley varies in response to the pivoting of the counter balancing link with respect to the first set-up joint to modify the tension in the at least one cable under tension to balance out changes in moment and mechanical advantage at the pivot point between the counter balancing link and the first set-up joint due to the pivoting of the counter balancing link and the load at the second set-up joint.

3. The set-up arm of claim 1, wherein the at least one cable under tension is coupled to the set up arm by coupling to the counter balancing link, the first set-up joint, or the second set-up joint.

4. The set-up arm of claim 1, wherein
the at least one cable under tension is coupled to the set up arm by wrapping over a post coupled to the counter balancing link,
the at least one cable under tension is twice wrapped over the plurality of pulleys, and
the at least one cable under tension has a pair of ends coupled to the second end of the first compression spring.

5. The set-up arm of claim 1, wherein
the at least one cable under tension is a plurality of cables under tension each of which has a substantially similar tension to share the total tension generated by the compression of the first compression spring.

6. The set-up arm of claim 1, wherein
the hollow housing has a first diagonally cut end and a second diagonally cut end opposite the first diagonally cut end, the first diagonally cut end and the second diagonally cut end to increase movement of the counter balancing link about the first set-up joint and the second set-up joint, respectively.

7. The set-up arm of claim 1, wherein
each of the plurality of pulleys has a substantially similar diameter.

8. A set-up arm to support a robotic arm, the set-up arm comprising:
a first set-up joint to couple to a support structure, the first set-up joint having a first pulley rotatably coupled thereto;
a second set-up joint spaced apart from the first set-up joint, the second set-up joint to couple to a robotic arm to provide support thereto;
a counter balancing link pivotally coupled to the first set-up joint at a first pivot point and to the second set-up joint at a second pivot point, the counter balancing link to balance out the force of load at the second set-up joint, the counter balancing link including
a hollow housing having a cylindrical cavity with a first opening at a first end,
a second pulley rotatably coupled to the hollow housing,
a first compression spring in the cylindrical cavity having a first end coupled to the housing, the first compression spring under compression to balance out the force of load at the second set-up joint; and
a third pulley having a center point at the first pivot point between the counter balancing link and the first set-up joint, wherein center point positions of the first, second, and third pulleys are corners of a triangle;
and
at least one cable under tension wrapped over the second pulley into the cylindrical cavity and coupled to a second end of the first compression spring, the at least one cable under tension further wrapped over the first and third pulleys and coupled to the set-up arm;
and wherein
each of the first, second, and third pulleys have a substantially similar diameter,
a first linear distance between the first pulley and the second pulley to vary in response to a pivoting of the counter balancing link at the first pivot point with the first set-up joint;
a second linear distance between the first pulley and the third pulley to remain constant in response to the pivoting of the counter balancing link at the first pivot point with the first set-up joint; and
a third linear distance between the second pulley and the third pulley to remain constant in response to the pivoting of the counter balancing link at the first pivot point with the first set-up joint.

9. A set-up arm to support a robotic arm, the set-up arm comprising:
a first set-up joint to couple to a support structure, the first set-up joint having a first pulley rotatably coupled thereto;
a second set-up joint spaced apart from the first set-up joint, the second set-up joint to couple to a robotic arm to provide support thereto;
a counter balancing link pivotally coupled to the first set-up joint at a first pivot point and to the second set-up joint at a second pivot point, the counter balancing link to balance out the force of load at the second set-up joint, the counter balancing link including
a hollow housing having a cylindrical cavity with a first opening at a first end
a plug coupled into the first opening to close the cylindrical cavity at the first end to increase stiffness of the counter balancing link,
a second pulley rotatable coupled to the hollow housing,
a first compression spring in the cylindrical cavity having a first end coupled to the housing, the first compression spring under compression to balance out the force of load at the second set-up joint; and
a third pulley having a center point at the first pivot point between the counter balancing link and the first set-up joint, wherein center point positions of the first, second, and third pulleys are corners of a triangle;
and
at least one cable under tension wrapped over the second pulley into the cylindrical cavity and coupled to a second end of the first compression spring, the at least one cable under tension further wrapped over the first and third pulleys and coupled to the set-up arm.

10. The set-up arm of claim 9, further comprising:
an idle link pivotally coupled to the first set-up joint at a third pivot point and to the second set-up joint at a fourth pivot point substantially parallel to the counter balancing link, the idle link to increase the stiffness in the set-up arm between the first set-up joint and the second set-up joint and the load carrying capability of the set-up arm.

11. The set-up arm of claim 10, wherein
the first set-up joint has a first bracket coupled to the idle and counter balancing links at the first and third pivot points respectively, the first bracket to allow the first set-up joint to rotate about a first axis; and the second set-up joint has a second bracket coupled to the idle and counter balancing links at the second and fourth pivot points respectively, the second bracket to allow the second set-up joint to rotate about a second axis.

12. The set-up arm of claim 10, wherein
the idle link and the counter balancing link are a parallel link, and
the first and third pivot points and the second and fourth pivot points spaced apart by the housing of the idle link and the housing of the counter balancing link to increase the torsional stiffness of the parallel link.

13. The set-up arm of claim 12, wherein
the counter balancing link further includes
 a clamping mechanism to couple the at least one cable under tension to the second end of the first compression spring.

14. The set-up arm of claim 13, wherein
the clamping mechanism includes
 a ribbonizer in a center opening of the first compression spring and coaxial thereto, the ribbonizer having a pair of slots at one end, and
 a clamping block coupled into the pair of slots of the ribbonizer, the clamping block to couple the at least one cable under tension to the first compression spring.

15. The set-up arm of claim 14, wherein
the clamping mechanism further includes
 a threaded sleeve around the ribbonizer coaxial with the compression spring, the threaded sleeve having an external thread, an end of the threaded sleeve coupled to a ridge of the ribbonizer,
 a nut having an internal thread threadingly engaged to the external thread of the threaded sleeve, the pre-tensioning nut to adjust the tension in the at least one cable under tension, and
 a mating ring over the threaded sleeve, the mating ring to receive a force from the nut and couple it to the first compression spring to adjust the tension in the at least one cable under tension.

16. The set-up arm of claim 15, wherein
the clamping mechanism further includes
 a thrust bearing over the threaded sleeve and coupled between the nut and the mating ring, the thrust bearing to receive a force from the nut and couple it to the mating ring.

17. The set-up arm of claim 16, wherein
the clamping mechanism further includes
 an anti-rotation plate having an opening over the clamping block and coupled to the ribbonizer, the anti-rotation plate having one or more protrusions coupled into one or more recesses in the cavity to deter the ribbonizer, the threaded sleeve and the clamping block from rotating as the nut is turned.

18. The set-up arm of claim 14, wherein
the clamping mechanism further includes
 one or more cable tensioners coupled between at least one end of the at least one cable under tension and the clamping block, the one or more cable tensioners to pre-tension the at least one cable under tension, each of the one or more cable tensioners including
  a second compression spring over the at least one cable under tension, and
  a cable terminator coupled to the at least one cable under tension near an end thereof.

19. The set-up arm of claim 14, wherein
the at least one cable under tension is a plurality of cables under tension, and
the clamping block includes
 a plurality of clamping plates stacked together, each of the plurality of clamping plates having a first opening, a second opening spaced apart from the first opening, and at least one groove to capture at least one cable segment of the plurality of cables under tension;
 a first fastener inserted into the first opening in each of the plurality of clamping plates; and
 a second fastener inserted into the second opening in each of the plurality of clamping plates; and
 wherein the first fastener and the second fastener squeeze the plurality of clamping plates together around the cable segments to clamp thereon with a substantial force.

20. The set-up arm of claim 19, wherein
the plurality of clamping plates includes
 a first outer clamping plate having the at least one groove in a top side;
 one or more interior clamping plates over the first outer clamping plate, each of the one or more interior clamping plates having at least one first groove in a top side and at least one second groove in a bottom side, one interior clamping plate having its at least one second groove aligned over the at least one groove in the first outer clamping plate; and
 a second outer clamping plate having the at least one groove in a bottom side, the at least one groove in the second outer clamping plate aligned over the at least one first groove in one interior clamping plate.

21. The set-up arm of claim 20, wherein
the plurality of cables have a substantially similar diameter, and
a depth of each of the at least one groove in the plurality of clamping plates is less than half the diameter of the plurality of cables.

22. The set-up arm of claim 20, wherein
the first and second openings in the first outer clamping plate are threaded to threadingly couple to the first and second fasteners respectively to squeeze the plurality of clamping plates together around the cable segments to clamp thereon with a substantial force.

23. The set-up arm of claim 20, wherein
the first opening in the first outer clamping plate is threaded to threadingly couple to the first fastener,
the second opening in the second outer clamping plate is threaded to threadingly couple to the second fastener, and
wherein the first fastener and the second fastener from opposite sides squeeze the plurality of clamping plates together around the cable segments to clamp thereon with a substantial force.

24. The set-up arm of claim 19, wherein
the plurality of cables under tension are routed substantially in parallel together, and
the at least one groove in each of the plurality of clamping plates is a pair of grooves substantially in parallel to capture cable segments of the plurality of cables under tension.

25. The set-up arm of claim 1, wherein
a first wrap angle of the at least one cable under tension around the first pulley to decrease to pay out cable and slightly compensate for an increase in the linear distance between the pair of pulleys in response to a first pivoting of the counter balancing link with respect to the first set-up joint; and
the first wrap angle to increase to pull in cable and slightly compensate for a decrease in the linear distance between the pair of pulleys in response to a second pivoting of the counter balancing link with respect to the first set-up joint in a direction opposite that of the first pivoting.

26. The set-up arm of claim 1, wherein
a total cable length of the at least one cable under tension is constant while the cable path length varies to modify the spring force and the tension in the at least one cable under tension in response to the pivoting of the counter balancing link with respect to the first set-up joint.

27. The set-up arm of claim 26, wherein
a sum total of wrap angles of the at least one cable under tension around the plurality of pulleys is conserved to remain constant in response to the pivoting of the counter balancing link with respect to the first set-up joint.

28. The set-up arm of claim 1, further comprising:
an idle link pivotally coupled to the first set-up joint at a third pivot point and to the second set-up joint at a fourth pivot point parallel to the counter balancing link.

29. The set-up arm of claim 2, further comprising:
an idle link pivotally coupled to the first set-up joint at a third pivot point and to the second set-up joint at a fourth pivot point parallel to the counter balancing link.

30. The set-up arm of claim 6, further comprising:
an idle link pivotally coupled to the first set-up joint at a third pivot point and to the second set-up joint at a fourth pivot point parallel to the counter balancing link.

31. The set-up arm of claim 6, wherein
the at least one cable under tension is further coupled to the set up arm.

32. The set-up arm of claim 6, wherein
the at least one cable under tension is a plurality of cables under tension each of which has a substantially similar tension to share the total tension generated therein by the spring.

33. The set-up arm of claim 8, further comprising:
an idle link pivotally coupled to the first set-up joint at a third pivot point and to the second set-up joint at a fourth pivot point parallel to the counter balancing link.

* * * * *